(12) United States Patent
Power et al.

(10) Patent No.: US 8,616,195 B2
(45) Date of Patent: Dec. 31, 2013

(54) NEBULISER FOR THE PRODUCTION OF AEROSOLIZED MEDICATION

(75) Inventors: John S Power, Moyculleu (IE); Declan Moran, County Galway (IE); Donal Devery, County Galway (IE); Gavan O'Sullivan, County Galway (IE); James Fink, San Matco, CA (US); Niall Smith, Galway (IE)

(73) Assignee: Novartis AG, Basel (CH)

( * ) Notice: Subject to any disclaimer, the term of this patent is extended or adjusted under 35 U.S.C. 154(b) by 2301 days.

(21) Appl. No.: 10/833,932

(22) Filed: Apr. 27, 2004

(65) Prior Publication Data

US 2005/0011514 A1    Jan. 20, 2005

Related U.S. Application Data

(60) Provisional application No. 60/488,718, filed on Jul. 18, 2003.

(51) Int. Cl.
*A61M 11/00* (2006.01)
*B05B 17/06* (2006.01)

(52) U.S. Cl.
USPC ........... 128/200.16; 128/200.14; 128/203.12; 128/203.15; 128/200.24

(58) Field of Classification Search
USPC ............ 128/200.14, 200.16, 200.18, 200.21, 128/203.12, 203.18, 203.22, 203.26, 204.14
See application file for complete search history.

(56) References Cited

U.S. PATENT DOCUMENTS

| | | |
|---|---|---|
| 550,315 A | 11/1895 | Allen |
| 809,159 A | 1/1906 | Willis et al. |
| 1,680,616 A | 8/1928 | Horst |
| 2,022,520 A | 11/1935 | Philbrick |
| 2,101,304 A | 12/1937 | Wright |
| 2,158,615 A | 5/1939 | Wright |
| 2,187,528 A | 1/1940 | Wing |
| 2,223,541 A | 12/1940 | Baker |
| 2,266,706 A | 12/1941 | Fox et al. |
| 2,283,333 A | 5/1942 | Martin |
| 2,292,381 A | 8/1942 | Klagges |
| 2,360,297 A | 10/1944 | Wing |

(Continued)

FOREIGN PATENT DOCUMENTS

| | | |
|---|---|---|
| CH | 477 885 | 9/1969 |
| CH | 555 681 | 11/1974 |

(Continued)

OTHER PUBLICATIONS

Abys, J.A. et al., "Annealing Behavior of Palladium-Nickel Alloy Electrodeposits," Plating and Surface Finishing, Aug. 1996, pp. 1-7.

(Continued)

*Primary Examiner* — Annette Dixon
(74) *Attorney, Agent, or Firm* — Janah & Associates, PC

(57) ABSTRACT

A nebulizer to deliver a medicament that includes a housing having a reservoir for the medicament, an aerosol generator that can be supplied the medicament from the reservoir, where the generator aerosolizes at least a portion of the medicament into an aerosol, a gas venting inlet to permit a gas to enter the nebulizer and form a mixture with the aerosol, and a passage through which the mixture of the aerosol and the gas is delivered to an outlet port of the nebulizer.

37 Claims, 17 Drawing Sheets

(56) References Cited

U.S. PATENT DOCUMENTS

| | | |
|---|---|---|
| 2,375,770 A | 5/1945 | Dahlberg |
| 2,383,098 A | 8/1945 | Wheaton |
| 2,404,063 A | 7/1946 | Healy |
| 2,430,023 A | 11/1947 | Longmaid |
| 2,474,996 A | 7/1949 | Wallis |
| 2,512,004 A | 6/1950 | Wing |
| 2,521,657 A | 9/1950 | Severy |
| 2,681,041 A | 6/1954 | Zodtner et al. |
| 2,705,007 A | 3/1955 | Gerber |
| 2,735,427 A | 2/1956 | Sullivan |
| 2,764,946 A | 10/1956 | Henderson |
| 2,764,979 A | 10/1956 | Henderson |
| 2,779,623 A | 1/1957 | Eisenkraft |
| 2,935,970 A | 5/1960 | Morse et al. |
| 3,103,310 A | 9/1963 | Lang |
| 3,325,031 A | 6/1967 | Singler |
| 3,411,854 A | 11/1968 | Rosler et al. |
| 3,515,348 A | 6/1970 | Coffman, Jr. |
| 3,550,864 A | 12/1970 | East |
| 3,558,052 A | 1/1971 | Dunn |
| 3,561,444 A | 2/1971 | Boucher |
| 3,563,415 A | 2/1971 | Ogle |
| 3,680,954 A | 8/1972 | Frank |
| 3,719,328 A | 3/1973 | Hindman |
| 3,738,574 A | 6/1973 | Guntersdorfer et al. |
| 3,771,982 A | 11/1973 | Dobo |
| 3,790,079 A | 2/1974 | Berglund et al. |
| 3,804,329 A | 4/1974 | Martner |
| 3,812,854 A | 5/1974 | Michaels et al. |
| 3,838,686 A | 10/1974 | Szekely |
| 3,842,833 A | 10/1974 | Ogle |
| 3,865,106 A | 2/1975 | Palush |
| 3,903,884 A | 9/1975 | Huston et al. |
| 3,906,950 A | 9/1975 | Cocozza |
| 3,908,654 A | 9/1975 | Lhoest et al. |
| 3,950,760 A | 4/1976 | Rauch et al. |
| 3,951,313 A | 4/1976 | Coniglione |
| 3,958,249 A | 5/1976 | DeMaine et al. |
| 3,970,250 A | 7/1976 | Drews |
| 3,983,740 A | 10/1976 | Danel |
| 3,993,223 A | 11/1976 | Welker, III et al. |
| 4,005,435 A | 1/1977 | Lundquist et al. |
| 4,030,492 A | 6/1977 | Simbruner |
| 4,052,986 A | 10/1977 | Scaife |
| 4,059,384 A | 11/1977 | Holland et al. |
| D246,574 S | 12/1977 | Meierhoefer |
| 4,076,021 A | 2/1978 | Thompson |
| 4,083,368 A | 4/1978 | Freezer |
| 4,094,317 A | 6/1978 | Wasnich |
| 4,101,041 A | 7/1978 | Mauro, Jr. et al. |
| 4,106,503 A | 8/1978 | Rosenthal et al. |
| 4,109,174 A | 8/1978 | Hodgson |
| 4,113,809 A | 9/1978 | Abair et al. |
| D249,958 S | 10/1978 | Meierhoefer |
| 4,119,096 A | 10/1978 | Drews |
| 4,121,583 A | 10/1978 | Chen |
| 4,159,803 A | 7/1979 | Cameto et al. |
| 4,207,990 A | 6/1980 | Weiler et al. |
| 4,210,155 A | 7/1980 | Grimes |
| 4,226,236 A | 10/1980 | Genese |
| 4,240,081 A | 12/1980 | Devitt |
| 4,240,417 A | 12/1980 | Holever |
| 4,248,227 A | 2/1981 | Thomas |
| 4,261,512 A | 4/1981 | Zierenberg |
| D259,213 S | 5/1981 | Pagels |
| 4,268,460 A | 5/1981 | Boiarski et al. |
| 4,294,407 A | 10/1981 | Reichl et al. |
| 4,298,045 A | 11/1981 | Weiler et al. |
| 4,299,784 A | 11/1981 | Hense |
| 4,300,546 A | 11/1981 | Kruber |
| 4,301,093 A | 11/1981 | Eck |
| 4,319,155 A | 3/1982 | Makai et al. |
| 4,334,531 A | 6/1982 | Reichl et al. |
| 4,336,544 A | 6/1982 | Donald et al. |
| 4,338,576 A | 7/1982 | Takahashi et al. |
| 4,368,476 A | 1/1983 | Uehara et al. |
| 4,368,850 A | 1/1983 | Szekely |
| 4,374,707 A | 2/1983 | Pollack |
| 4,389,071 A | 6/1983 | Johnson, Jr. et al. |
| 4,408,719 A | 10/1983 | Last |
| 4,428,802 A | 1/1984 | Kanai et al. |
| 4,431,136 A | 2/1984 | Janner et al. |
| 4,454,877 A | 6/1984 | Miller et al. |
| 4,465,234 A | 8/1984 | Maehara et al. |
| 4,474,251 A | 10/1984 | Johnson, Jr. |
| 4,474,326 A | 10/1984 | Takahashi |
| 4,475,113 A | 10/1984 | Lee et al. |
| 4,479,609 A | 10/1984 | Maeda et al. |
| 4,512,341 A | 4/1985 | Lester |
| 4,530,464 A | 7/1985 | Yamamoto et al. |
| 4,533,082 A | 8/1985 | Maehara et al. |
| 4,539,575 A | 9/1985 | Nilsson |
| 4,544,933 A | 10/1985 | Heinzl |
| 4,546,361 A | 10/1985 | Brescia et al. |
| 4,550,325 A | 10/1985 | Viola |
| 4,566,452 A | 1/1986 | Farr |
| 4,582,654 A | 4/1986 | Karnicky et al. |
| 4,591,883 A | 5/1986 | Isayama |
| 4,593,291 A | 6/1986 | Howkins |
| 4,605,167 A | 8/1986 | Maehara |
| 4,613,326 A | 9/1986 | Szwarc |
| 4,620,201 A | 10/1986 | Heinzl et al. |
| 4,628,890 A | 12/1986 | Freeman |
| 4,632,311 A | 12/1986 | Nakane et al. |
| 4,658,269 A | 4/1987 | Rezanka |
| 4,659,014 A | 4/1987 | Soth et al. |
| 4,677,975 A | 7/1987 | Edgar et al. |
| 4,678,680 A | 7/1987 | Abowitz |
| 4,679,551 A | 7/1987 | Anthony |
| 4,681,264 A | 7/1987 | Johnson, Jr. |
| 4,693,853 A | 9/1987 | Falb et al. |
| 4,702,418 A | 10/1987 | Carter et al. |
| 4,722,906 A | 2/1988 | Guire |
| 4,753,579 A | 6/1988 | Murphy |
| 4,790,479 A | 12/1988 | Matsumoto et al. |
| 4,793,339 A | 12/1988 | Matsumoto et al. |
| 4,796,807 A | 1/1989 | Bendig et al. |
| 4,799,622 A | 1/1989 | Ishikawa et al. |
| 4,805,609 A | 2/1989 | Roberts et al. |
| 4,819,629 A | 4/1989 | Jonson |
| 4,819,834 A | 4/1989 | Thiel |
| 4,826,080 A | 5/1989 | Ganser |
| 4,826,759 A | 5/1989 | Guire et al. |
| 4,828,886 A | 5/1989 | Hieber |
| 4,843,445 A | 6/1989 | Stemme |
| 4,849,303 A | 7/1989 | Graham et al. |
| 4,850,534 A | 7/1989 | Takahashi et al. |
| 4,865,006 A | 9/1989 | Nogi et al. |
| 4,871,489 A | 10/1989 | Ketcham |
| 4,872,553 A | 10/1989 | Suzuki et al. |
| 4,877,989 A | 10/1989 | Drews et al. |
| 4,888,516 A | 12/1989 | Daeges et al. |
| 4,922,901 A | 5/1990 | Brooks et al. |
| 4,926,915 A | 5/1990 | Deussen et al. |
| 4,934,358 A | 6/1990 | Nilsson et al. |
| 4,954,225 A | 9/1990 | Bakewell |
| 4,957,239 A | 9/1990 | Tempelman |
| 4,964,521 A | 10/1990 | Wieland et al. |
| D312,209 S | 11/1990 | Morrow et al. |
| 4,968,299 A | 11/1990 | Ahlstrand et al. |
| 4,971,665 A | 11/1990 | Sexton |
| 4,973,493 A | 11/1990 | Guire |
| 4,976,259 A * | 12/1990 | Higson et al. ............ 128/200.18 |
| 4,979,959 A | 12/1990 | Guire |
| 4,993,411 A * | 2/1991 | Callaway ................. 128/204.14 |
| 4,994,043 A | 2/1991 | Ysebaert |
| 5,002,048 A | 3/1991 | Makiej, Jr. |
| 5,002,582 A | 3/1991 | Guire et al. |
| 5,007,419 A | 4/1991 | Weinstein et al. |
| 5,016,024 A | 5/1991 | Lam et al. |
| 5,021,701 A | 6/1991 | Takahashi et al. |
| 5,022,587 A | 6/1991 | Hochstein |
| 5,024,733 A | 6/1991 | Abys et al. |
| 5,046,627 A | 9/1991 | Hansen |

(56) References Cited

U.S. PATENT DOCUMENTS

| | | | |
|---|---|---|---|
| 5,062,419 A | 11/1991 | Rider | |
| 5,063,396 A | 11/1991 | Shiokawa et al. | |
| 5,063,921 A * | 11/1991 | Howe | 128/200.14 |
| 5,063,922 A | 11/1991 | Häkkinen | |
| 5,073,484 A | 12/1991 | Swanson et al. | |
| 5,076,266 A | 12/1991 | Babaev | |
| 5,080,093 A | 1/1992 | Raabe et al. | |
| 5,080,649 A | 1/1992 | Vetter | |
| 5,086,765 A | 2/1992 | Levine | |
| 5,086,785 A | 2/1992 | Gentile et al. | |
| 5,115,803 A | 5/1992 | Sioutas | |
| 5,115,971 A | 5/1992 | Greenspan et al. | |
| D327,008 S | 6/1992 | Friedman | |
| 5,122,116 A | 6/1992 | Kriesel et al. | |
| 5,129,579 A | 7/1992 | Conte | |
| 5,134,993 A | 8/1992 | Van der Linden et al. | |
| 5,139,016 A | 8/1992 | Waser | |
| 5,140,740 A | 8/1992 | Weigelt | |
| 5,147,073 A | 9/1992 | Cater | |
| 5,152,456 A | 10/1992 | Ross et al. | |
| 5,157,372 A | 10/1992 | Langford | |
| 5,164,740 A | 11/1992 | Ivri | |
| 5,169,029 A | 12/1992 | Behar et al. | |
| 5,170,782 A | 12/1992 | Kocinski | |
| 5,180,482 A | 1/1993 | Abys et al. | |
| 5,186,164 A | 2/1993 | Raghuprasad | |
| 5,186,166 A | 2/1993 | Riggs et al. | |
| 5,198,157 A | 3/1993 | Bechet | |
| 5,201,322 A | 4/1993 | Henry et al. | |
| 5,213,860 A | 5/1993 | Laing | |
| 5,217,148 A | 6/1993 | Cater | |
| 5,217,492 A | 6/1993 | Guire et al. | |
| 5,227,168 A | 7/1993 | Chvapil et al. | |
| 5,230,496 A | 7/1993 | Shillington et al. | |
| 5,245,995 A | 9/1993 | Sullivan et al. | |
| 5,248,087 A | 9/1993 | Dressler | |
| 5,258,041 A | 11/1993 | Guire et al. | |
| 5,261,601 A | 11/1993 | Ross et al. | |
| 5,263,992 A | 11/1993 | Guire | |
| 5,279,568 A | 1/1994 | Cater | |
| 5,297,734 A | 3/1994 | Toda | |
| 5,299,739 A | 4/1994 | Takahashi et al. | |
| 5,303,854 A | 4/1994 | Cater | |
| 5,309,135 A | 5/1994 | Langford | |
| 5,312,281 A * | 5/1994 | Takahashi et al. | 446/25 |
| 5,313,955 A | 5/1994 | Rodder | |
| 5,319,971 A | 6/1994 | Osswald et al. | |
| 5,320,603 A | 6/1994 | Vetter et al. | |
| 5,322,057 A | 6/1994 | Raabe et al. | |
| 5,342,011 A | 8/1994 | Short | |
| 5,342,504 A | 8/1994 | Hirano et al. | |
| 5,347,998 A | 9/1994 | Hodson et al. | |
| 5,348,189 A | 9/1994 | Cater | |
| 5,350,116 A | 9/1994 | Cater | |
| 5,355,872 A | 10/1994 | Riggs et al. | |
| 5,357,946 A | 10/1994 | Kee et al. | |
| 5,372,126 A | 12/1994 | Blau | |
| 5,383,906 A | 1/1995 | Burchett et al. | |
| 5,388,571 A | 2/1995 | Roberts et al. | |
| 5,388,574 A | 2/1995 | Ingebrethsen | |
| 5,392,768 A | 2/1995 | Johansson et al. | |
| 5,396,883 A | 3/1995 | Knupp et al. | |
| 5,414,075 A | 5/1995 | Swan et al. | |
| 5,415,161 A | 5/1995 | Ryder | |
| 5,419,315 A | 5/1995 | Rubsamen | |
| 5,426,458 A | 6/1995 | Wenzel et al. | |
| 5,431,155 A | 7/1995 | Marelli | |
| 5,435,282 A * | 7/1995 | Haber et al. | 128/200.16 |
| 5,435,297 A | 7/1995 | Klein | |
| 5,437,267 A | 8/1995 | Weinstein et al. | |
| 5,445,141 A | 8/1995 | Kee et al. | |
| D362,390 S | 9/1995 | Weiler | |
| 5,449,502 A | 9/1995 | Igusa et al. | |
| 5,452,711 A | 9/1995 | Gault | |
| 5,458,135 A | 10/1995 | Patton et al. | |
| 5,458,289 A | 10/1995 | Cater | |
| 5,474,059 A | 12/1995 | Cooper | |
| 5,477,992 A | 12/1995 | Jinks et al. | |
| 5,479,920 A | 1/1996 | Piper et al. | |
| 5,487,378 A * | 1/1996 | Robertson et al. | 128/200.16 |
| 5,489,266 A | 2/1996 | Grimard | |
| 5,497,944 A | 3/1996 | Weston et al. | |
| D369,212 S | 4/1996 | Snell | |
| 5,511,726 A | 4/1996 | Greenspan et al. | |
| 5,512,329 A | 4/1996 | Guire et al. | |
| 5,512,474 A | 4/1996 | Clapper et al. | |
| 5,515,841 A | 5/1996 | Robertson et al. | |
| 5,515,842 A | 5/1996 | Ramseyer et al. | |
| 5,516,043 A | 5/1996 | Manna et al. | |
| 5,518,179 A | 5/1996 | Humberstone et al. | |
| 5,529,055 A | 6/1996 | Gueret | |
| 5,533,497 A | 7/1996 | Ryder | |
| 5,542,410 A | 8/1996 | Goodman et al. | |
| 5,549,102 A | 8/1996 | Lintl et al. | |
| 5,551,416 A | 9/1996 | Stimpson et al. | |
| 5,560,837 A | 10/1996 | Trueba | |
| 5,563,056 A | 10/1996 | Swan et al. | |
| D375,352 S | 11/1996 | Bologna | |
| 5,579,757 A | 12/1996 | McMahon et al. | |
| 5,582,330 A | 12/1996 | Iba | |
| 5,584,285 A | 12/1996 | Salter et al. | |
| 5,586,550 A | 12/1996 | Ivri et al. | |
| 5,588,166 A | 12/1996 | Burnett | |
| 5,601,077 A | 2/1997 | Imbert | |
| 5,609,798 A | 3/1997 | Liu et al. | |
| 5,632,878 A | 5/1997 | Kitano | |
| 5,635,096 A | 6/1997 | Singer et al. | |
| 5,637,460 A | 6/1997 | Swan et al. | |
| 5,647,349 A | 7/1997 | Ohki et al. | |
| 5,653,227 A | 8/1997 | Barnes et al. | |
| 5,654,007 A | 8/1997 | Johnson et al. | |
| 5,654,162 A | 8/1997 | Guire et al. | |
| 5,654,460 A | 8/1997 | Rong | |
| 5,657,926 A | 8/1997 | Toda | |
| 5,660,166 A | 8/1997 | Lloyd | |
| 5,664,557 A | 9/1997 | Makiej, Jr. | |
| 5,664,706 A | 9/1997 | Cater | |
| 5,665,068 A | 9/1997 | Takamura | |
| 5,666,946 A | 9/1997 | Langenback | |
| 5,670,999 A | 9/1997 | Takeuchi et al. | |
| 5,685,491 A | 11/1997 | Marks et al. | |
| 5,692,644 A | 12/1997 | Gueret | |
| 5,707,818 A | 1/1998 | Chudzik et al. | |
| 5,709,202 A | 1/1998 | Lloyd et al. | |
| 5,714,360 A | 2/1998 | Swan et al. | |
| 5,714,551 A | 2/1998 | Bezwada et al. | |
| 5,718,222 A | 2/1998 | Lloyd et al. | |
| D392,184 S | 3/1998 | Weiler | |
| 5,724,957 A | 3/1998 | Rubsamen et al. | |
| 5,744,515 A | 4/1998 | Clapper | |
| 5,752,502 A | 5/1998 | King | |
| 5,755,218 A | 5/1998 | Johansson et al. | |
| 5,758,637 A * | 6/1998 | Ivri et al. | 128/200.16 |
| 5,775,506 A | 7/1998 | Grabenkort | |
| 5,788,665 A | 8/1998 | Sekins | |
| 5,788,819 A | 8/1998 | Onishi et al. | |
| 5,790,151 A | 8/1998 | Mills | |
| 5,810,004 A | 9/1998 | Ohki et al. | |
| 5,819,730 A | 10/1998 | Stone et al. | |
| 5,823,179 A | 10/1998 | Grychowski et al. | |
| 5,823,428 A | 10/1998 | Humberstone et al. | |
| 5,829,723 A | 11/1998 | Brunner et al. | |
| 5,836,515 A | 11/1998 | Fonzes | |
| 5,839,617 A | 11/1998 | Cater et al. | |
| 5,842,468 A | 12/1998 | Denyer et al. | |
| 5,862,802 A | 1/1999 | Bird | |
| 5,865,171 A | 2/1999 | Cinquin | |
| 5,878,900 A | 3/1999 | Hansen | |
| 5,893,515 A | 4/1999 | Hahn et al. | |
| 5,894,841 A | 4/1999 | Voges | |
| 5,897,008 A | 4/1999 | Hansen | |
| 5,910,698 A | 6/1999 | Yagi | |
| 5,915,377 A | 6/1999 | Coffee | |
| 5,918,637 A | 7/1999 | Fleischman | |

(56) References Cited

U.S. PATENT DOCUMENTS

| | | | |
|---|---|---|---|
| 5,925,019 A | 7/1999 | Ljungquist | |
| 5,938,117 A | 8/1999 | Ivri | |
| 5,950,619 A | 9/1999 | Van der Linden et al. | |
| 5,954,268 A | 9/1999 | Joshi et al. | |
| 5,960,792 A | 10/1999 | Lloyd et al. | |
| 5,964,417 A | 10/1999 | Amann et al. | |
| 5,970,974 A | 10/1999 | Van Der Linden et al. | |
| 5,976,344 A | 11/1999 | Abys et al. | |
| 5,993,805 A | 11/1999 | Sutton et al. | |
| 6,000,396 A | 12/1999 | Melker et al. | |
| 6,007,518 A | 12/1999 | Kriesel et al. | |
| 6,012,450 A | 1/2000 | Rubsamen | |
| 6,014,970 A | 1/2000 | Ivri et al. | |
| 6,026,809 A | 2/2000 | Abrams et al. | |
| 6,029,666 A | 2/2000 | Aloy et al. | |
| 6,032,665 A | 3/2000 | Psaros | |
| 6,037,587 A | 3/2000 | Dowell et al. | |
| 6,039,696 A | 3/2000 | Bell | |
| 6,045,215 A | 4/2000 | Coulman | |
| 6,045,874 A | 4/2000 | Himes | |
| 6,047,818 A | 4/2000 | Warby et al. | |
| 6,055,869 A | 5/2000 | Stemme et al. | |
| 6,060,128 A | 5/2000 | Kim et al. | |
| 6,062,212 A | 5/2000 | Davison et al. | |
| 6,068,148 A | 5/2000 | Weiler | |
| 6,085,740 A | 7/2000 | Ivri et al. | |
| 6,096,011 A | 8/2000 | Trombley, III et al. | |
| 6,105,877 A | 8/2000 | Coffee | |
| 6,106,504 A | 8/2000 | Urrutia | |
| 6,116,234 A | 9/2000 | Genova et al. | |
| 6,123,413 A | 9/2000 | Agarwal et al. | |
| 6,139,674 A | 10/2000 | Markham et al. | |
| 6,142,146 A | 11/2000 | Abrams et al. | |
| 6,145,963 A | 11/2000 | Pidwerbecki et al. | |
| 6,146,915 A | 11/2000 | Pidwerbecki et al. | |
| 6,152,130 A | 11/2000 | Abrams et al. | |
| 6,155,676 A | 12/2000 | Etheridge et al. | |
| 6,158,431 A | 12/2000 | Poole | |
| 6,161,536 A | 12/2000 | Redmon et al. | |
| 6,163,588 A | 12/2000 | Matsumoto et al. | |
| 6,182,662 B1 | 2/2001 | McGhee | |
| 6,186,141 B1 | 2/2001 | Pike et al. | |
| 6,196,218 B1 | 3/2001 | Voges | |
| 6,196,219 B1 | 3/2001 | Hess et al. | |
| 6,205,999 B1 | 3/2001 | Ivri et al. | |
| 6,216,916 B1 | 4/2001 | Maddox et al. | |
| 6,223,746 B1 | 5/2001 | Jewett et al. | |
| 6,235,177 B1 | 5/2001 | Borland et al. | |
| 6,254,219 B1 | 7/2001 | Agarwal et al. | |
| 6,269,810 B1 | 8/2001 | Brooker et al. | |
| 6,270,473 B1 | 8/2001 | Schwebel | |
| 6,273,342 B1 | 8/2001 | Terada et al. | |
| 6,318,640 B1 | 11/2001 | Coffee | |
| 6,328,030 B1 | 12/2001 | Kidwell et al. | |
| 6,328,033 B1 | 12/2001 | Avrahami | |
| 6,341,732 B1 | 1/2002 | Martin et al. | |
| 6,358,058 B1 | 3/2002 | Strupat et al. | |
| 6,394,363 B1 | 5/2002 | Arnott et al. | |
| 6,402,046 B1 | 6/2002 | Loser | |
| 6,405,934 B1 | 6/2002 | Hess et al. | |
| 6,427,682 B1 | 8/2002 | Klimowicz et al. | |
| 6,443,146 B1 | 9/2002 | Voges | |
| 6,443,366 B1 | 9/2002 | Hirota et al. | |
| 6,467,476 B1 | 10/2002 | Ivri et al. | |
| 6,530,370 B1 | 3/2003 | Heinonen | |
| 6,540,153 B1 | 4/2003 | Ivri | |
| 6,540,154 B1 | 4/2003 | Ivri et al. | |
| 6,543,443 B1 | 4/2003 | Klimowicz et al. | |
| 6,546,927 B2 * | 4/2003 | Litherland et al. | 128/200.16 |
| 6,550,472 B2 | 4/2003 | Litherland et al. | |
| 6,554,201 B2 | 4/2003 | Klimowicz et al. | |
| 6,581,595 B1 | 6/2003 | Murdock et al. | |
| 6,615,824 B2 | 9/2003 | Power | |
| 6,629,646 B1 | 10/2003 | Ivri | |
| 6,640,804 B2 | 11/2003 | Ivri | |
| 6,651,650 B1 | 11/2003 | Yamamoto et al. | |
| 6,705,315 B2 | 3/2004 | Sullivan et al. | |
| 6,732,944 B2 | 5/2004 | Litherland et al. | |
| 6,745,768 B2 | 6/2004 | Colla et al. | |
| 6,745,770 B2 | 6/2004 | McAuliffe et al. | |
| 6,755,189 B2 | 6/2004 | Ivri et al. | |
| 6,769,626 B1 | 8/2004 | Haveri | |
| 6,782,886 B2 | 8/2004 | Narayan et al. | |
| 6,810,876 B2 | 11/2004 | Berthon-Jones | |
| 6,814,071 B2 | 11/2004 | Klimowicz et al. | |
| 6,817,361 B2 | 11/2004 | Berthon-Jones et al. | |
| 6,830,046 B2 * | 12/2004 | Blakley et al. | 128/200.14 |
| 6,840,240 B1 | 1/2005 | Berthon-Jones et al. | |
| 6,845,770 B2 | 1/2005 | Klimowicz et al. | |
| 6,851,626 B2 | 2/2005 | Patel et al. | |
| 6,860,268 B2 | 3/2005 | Bohn et al. | |
| 6,983,747 B2 * | 1/2006 | Gallem et al. | 128/203.12 |
| 7,059,320 B2 * | 6/2006 | Feiner et al. | 128/200.16 |
| 7,195,011 B2 * | 3/2007 | Loeffler et al. | 128/200.14 |
| 7,322,349 B2 * | 1/2008 | Power | 128/200.14 |
| 2001/0013554 A1 | 8/2001 | Borland et al. | |
| 2001/0015737 A1 | 8/2001 | Truninger et al. | |
| 2002/0011247 A1 | 1/2002 | Ivri et al. | |
| 2002/0023650 A1 | 2/2002 | Gunaratnam et al. | |
| 2002/0033178 A1 | 3/2002 | Farrell et al. | |
| 2002/0036601 A1 | 3/2002 | Puckeridge et al. | |
| 2002/0078958 A1 | 6/2002 | Stenzler | |
| 2002/0104530 A1 | 8/2002 | Ivri et al. | |
| 2002/0121274 A1 | 9/2002 | Borland et al. | |
| 2002/0134372 A1 | 9/2002 | Loeffler et al. | |
| 2002/0134374 A1 | 9/2002 | Loeffler et al. | |
| 2002/0134375 A1 | 9/2002 | Loeffler et al. | |
| 2002/0134377 A1 | 9/2002 | Loeffler et al. | |
| 2002/0162551 A1 | 11/2002 | Litherland | |
| 2003/0140921 A1 | 7/2003 | Smith et al. | |
| 2003/0145859 A1 | 8/2003 | Bohn et al. | |
| 2003/0150445 A1 | 8/2003 | Power et al. | |
| 2003/0150446 A1 | 8/2003 | Patel et al. | |
| 2003/0226906 A1 | 12/2003 | Ivri | |
| 2004/0000598 A1 | 1/2004 | Ivri | |
| 2004/0004133 A1 | 1/2004 | Ivri et al. | |
| 2004/0011358 A1 | 1/2004 | Smaldone et al. | |
| 2004/0035413 A1 | 2/2004 | Smaldone et al. | |
| 2004/0035490 A1 | 2/2004 | Power | |
| 2004/0050947 A1 | 3/2004 | Power et al. | |
| 2004/0139963 A1 | 7/2004 | Ivri et al. | |
| 2004/0139968 A1 | 7/2004 | Loeffler et al. | |
| 2004/0188534 A1 | 9/2004 | Litherland et al. | |
| 2004/0194783 A1 | 10/2004 | McAuliffe et al. | |
| 2004/0226561 A1 | 11/2004 | Colla et al. | |
| 2004/0226566 A1 | 11/2004 | Gunaratnam et al. | |
| 2004/0256488 A1 | 12/2004 | Loeffler et al. | |
| 2005/0284469 A1 | 12/2005 | Tobia et al. | |

FOREIGN PATENT DOCUMENTS

| | | |
|---|---|---|
| DE | 11 03 522 | 3/1961 |
| EP | 0 049 636 A1 | 4/1982 |
| EP | 0 103 161 A2 | 3/1984 |
| EP | 0 134 847 A1 | 3/1985 |
| EP | 0174862 A1 | 3/1986 |
| EP | 0 178 925 A2 | 4/1986 |
| EP | 0 387 222 A1 | 9/1990 |
| EP | 0 432 992 A1 | 6/1991 |
| EP | 0 476 991 B1 | 3/1992 |
| EP | 0 480 615 A1 | 4/1992 |
| EP | 0 510 648 A2 | 10/1992 |
| EP | 0 516 565 A1 | 12/1992 |
| EP | 0 542 723 A2 | 5/1993 |
| EP | 0 933 138 A2 | 4/1999 |
| EP | 0 923 957 A1 | 6/1999 |
| EP | 1 142 600 A1 | 10/2001 |
| GB | 973 458 | 10/1964 |
| GB | 1 454 597 | 11/1976 |
| GB | 2 073 616 A | 10/1981 |
| GB | 2 101 500 | 1/1983 |
| GB | 2 177 623 A | 1/1987 |
| GB | 2 240 494 A | 7/1991 |
| GB | 2 272 389 A | 5/1994 |

(56) References Cited

FOREIGN PATENT DOCUMENTS

| | | |
|---|---|---|
| JP | 57-023852 | 2/1982 |
| JP | 57-105608 | 7/1982 |
| JP | 58-061857 | 4/1983 |
| JP | 58-139757 | 8/1983 |
| JP | 59-142163 A | 8/1984 |
| JP | 60-004714 | 1/1985 |
| JP | 61-008357 A | 1/1986 |
| JP | 61-215059 A | 9/1986 |
| JP | 02-135169 | 5/1990 |
| JP | 02-189161 | 7/1990 |
| JP | 60-07721 A | 1/1994 |
| JP | 10-508251 | 8/1998 |
| JP | 2005277188 A | 10/2005 |
| WO | WO 82/03548 A | 10/1982 |
| WO | WO 92/07600 A1 | 5/1992 |
| WO | WO 92/11050 A1 | 9/1992 |
| WO | WO 92/17231 A1 | 10/1992 |
| WO | WO 93/01404 A1 | 1/1993 |
| WO | WO 93/10910 A1 | 6/1993 |
| WO | WO 94/09912 A1 | 5/1994 |
| WO | WO 96/09229 | 3/1996 |
| WO | WO 99/17888 | 4/1999 |
| WO | WO 00/37132 | 6/2000 |
| WO | WO0264265 | 1/2002 |
| WO | WO03041774 | 10/2002 |

OTHER PUBLICATIONS

Allen T. *Particle Size Measurement*, Third Edition, Chapman and Hall pp. 167-169 (1981).

Ashgriz, N. et al. "Development of a Controlled Spray Generator" Rev. Sci. Instrum., 1987, pp. 1291-1296, vol. 58, No. 7.

Berggren, E. "Pilot Study of Nebulized Surfactant Therapy for Neonatal Respiratory Distress Syndrome", Acta Paediatr 89: 460-464, Taylor & Francis, ISSN 0803-5253, 2000, Sweden.

Berglund, R.N., et al. "Generation of Monodisperse Aerosol Standards" Environ. Sci. Technology, Feb. 1973, pp. 147-153, vol. 7, No. 2.

Cipolla, D.C. et al., "Assessment of Aerosol Delivery Systems for Recombinant Human Deoxyribonuclease," S.T.P. Pharma Sciences 4 (1) 50-62, 1994.

Cipolla, D.C. et al., "Characterization of Aerosols of Human Recombinant Deoxyribonuclease I (rhDNase) Generated by Neulizers," Pharmaceutical Research II (4) 491-498, 1994.

Dogan, Aydin PhD, Thesis: "Flexional 'Moonie and Cymbal' Actuators", Penn State University, 1994.

Duarte, Alexander G. et al. "Inhalation Therapy During Mechanical Ventilation" Respiratory Care Clinics of North America, Aerosol Therapy, Jun. 2001, pp. 233-259, vol. 7, No. 2.

Fink, James B. et al. "Aerosol Drug Therapy," Clinical Practice in Respiratory Care; Chapter 12, pp. 308-342; 1999.

Fink, James B. et al. "Aerosol Therapy in Mechanically Ventilated Patients: Recent Advances and New Techniques" Seminars in Respiratory and Critical Care Medicine, 2000, pp. 183-201, vol. 21, No. 3.

Fink, James B. et al. Diagram from and abstract of article entitled "Optimizing efficiency of nebulizers during mechanical ventilation: The effect of placement and type of ventilator circuit" Chest, Oct. 1999, 116:312S.

Geiser Tool Company catalog, pp. 26, 29-30 (1990).

Gonda, I. "Therapeutic Aerosols," Pharmaceutics, The Science of Dosage Form Design, Editor: M.E. Aulton, 341-358, 1988.

Hancock, B.C. et al., "Molecular Mobility of Amorphous Pharmaceutical Solids Below Their Glass Transition Temperatures," Pharmaceutical Research 12, 799-806 (1995).

Heyder, J. et al., "Deposition of particles in the human respiratory tract in the size range 0.005-15 microns." J Aerosol Sci 17: 811-825, 1986.

Hickey, Anthony J. "Pharmaceutical Inhalation Aerosol Technology," Drugs and the Pharmaceutical Science, 1992, pp. 172-173, vol. 54.

Hikayama, H., et al. "Ultrasonic Atomizer with Pump Function" Tech. Rpt. IEICE Japan US88-74:25 (1988).

Jorch, G. Letter to the Editor, "Surfactant Aerosol Treatment of Respiratory Distress Syndrome in Spontaneously Breathing Premature Infants", Pediatric Pulmonology 24: 222-224, 1997, Wiley-Liss.

Maehara, N. et al. "Atomizing rate control of a multi-pinhole-plate ultrasonic atomizer" J. Acoustical Soc. Japan, 1988, pp. 116-121, 44:2.

Maehara, N. et al. "Influence of the vibrating system of a multipinhole-plate ultrasonic nebulizer on its performance" Review of Scientific Instruments, Nov. 1986, p. 2870-2876, vol. 57, No. 1.

Maehara, N. et al. "Influences of liquid's physical properties on the characteristics of a multi-pinhole-plate ultrasonic atomizer" J. Acoustical Soc. Japan 1988, pp. 425-431, 44:6.

Maehara, N. et al. "Optimum Design Procedure for Multi-Pinhole-Plate Ultrasonic Atomizer" Japanese Journal of Applied Physics, 1987, pp. 215-217, vol. 26, Supplement 26-1.

Nogi, T. et al. "Mixture Formation of Fuel Injection System in Gasoline Engine" Nippon Kikal Gakkai Zenkoku Taikai Koenkai Koen Ronbunshu 69:660-662 (1991).

Palla Tech Pd an Pd Alloy Processes—Procedure for the Analysis of Additive IVS in Palla Tech Plating Solutions by HPLC, Technical Bulletin, Electroplating Chemicals & Services, 029-A, Lucent Technologies,, pp. 1-5, 1996.

Siemens, "Servo Ultra Nebulizer 345 Operating Manual," pp. 1-23.

Smaldone, G. C. "Aerosolized Antibiotics: Current and Future", Respiratory Care, 2000, vol. 45, No. 6, pp. 667-675.

Smedsaas-Löfvenbert, A. "Nebulization of Drugs in a Nasal CPAP System", Scandinavian University Press, 1999, Acta Paediatr 88: 89-92, Sweden.

TSI Incorporated product catalog. Vibrating Orifice Aerosol Generator (1989).

Ueha, S., et al. "Mechanism of Ultrasonic Atomization Using a Multi-Pinhole Plate" J. Acoust. Soc. Jpn., 1985, pp. 21-26, (E)6,1.

Wehl, Wolfgang R. "Ink-Jet Printing: The Present State of the Art" for Siemens AG, 1989.

* cited by examiner

NEBULISER FOR THE PRODUCTION OF AEROSOLIZED MEDICATION

CROSS-REFERENCES TO RELATED APPLICATIONS

This application claims the benefit of U.S. Provisional Application No. 60/488,718, filed Jul. 18, 2003, which is incorporated herein by reference in its entirety.

BACKGROUND OF THE INVENTION

This invention relates to a nebuliser for delivery of medicament to the respiratory system of a patient. Certain conditions such as asthma, chronic obstructive pulmonary disease (COPD), and cystic fibrosis require that prescribed liquid medication be turned into a fine mist, called an aerosol, and then inhaled into the lungs.

Nebulisers for creating such an aerosol of medication are known. However, conventional nebulisers for home use are generally large and bulky and are inconvenient to use. Thus, there is a need for compact nebulisers that are more convenient for use at home.

Nebulisers have long been used to produce aerosols. There are three major classifications of nebulisers for home use. Compressor driven jet or pneumatic nebulisers utilise a reservoir in which medication is placed below the point of aerosol generation, so that medication is drawn up from the reservoir by the action of the jet, which then shears the fluid into small particles. Aerosol collects in and passes through a chamber above the medication reservoir, driven by the flow of gas that generates the aerosol. This constant flow of aerosol from the nebuliser often exceeds inspiratory flows and volumes generated by the patient and reduces the amount of aerosol available for inspiration, reducing the mass of drug inhaled by the patient. Thus, there remains a need for nebulisers that reduce the amount of flow gas needed to deliver aerosolized medication to a patient.

Ultrasonic nebulisers create standing waves in a medication reservoir, above a peizo ceramic element, generating aerosol that collects above the medication reservoir. Aerosol does not leave the collection chamber without active gas flow generated directly by the patient, or by a secondary flow of gas (e.g., fan). This reduces the ability of the ultrasonic to be used with an open aerosol mask. Thus there remains a need for nebulisers that can be used with an open aerosol mask.

In both jet and ultrasonic nebulisers droplets that do not leave the aerosol chamber remain on the walls of the chamber or return to the reservoir, contributing to a residual drug remaining in the nebuliser. Thus there remains a need for nebulisers that reduce the amount of residual drug that remains in the nebulizer.

A nebuliser is also known which has a medication reservoir connected to a transducer horn placed below a mesh plate. The vibration of the horn pushes the liquid medication through orifices in the mesh plate placed above it. Aerosol is directed up from the aerosol generator. Technical limitations of this technology result in relatively large particle sizes, low output, difficulty in aerosolizing suspensions, and a lack of reservoir to effectively collect aerosol between inspiratory efforts. Thus, there remains a need for nebulizers that generate fine aerosol mists with high output, and which also have a reservoir to collect aerosol between inspiratory efforts.

BRIEF SUMMARY OF THE INVENTION

The present invention includes a nebuliser for delivery of a medicament to a patient's respiratory system. The nebuliser may include a housing that forms a reservoir for a liquid medicament. The medicament may enter the reservoir through an inlet and exit the reservoir through an outlet coupled to an aerosol generator. The generator converts the medicament into an aerosol that may travel through an aerosol passage to an outlet port where the aerosol exits the nebuliser. The nebuliser may also include a gas venting inlet that allows gas (e.g., air) to enter the nebuliser and mix with the aerosolized medicament before the mixture of gas and entrained aerosol exits the nebuliser through the outlet port.

In one embodiment gravitational flow of a liquid medicament is supplied from the reservoir to the aerosol generator.

The gas venting inlet may be located in close proximity to the aerosol generator.

In another embodiment the housing has a baffle to direct gas and entrained aerosol to the outlet port. Said baffle may include an inclined surface oriented to cause aerosol to flow through the outlet. The baffle may be inclined towards the outlet port.

In another embodiment the nebuliser may include an aerosol rainout trap. The rainout trap may be adjacent to the outlet port.

In another embodiment the nebuliser may include an aerosol trap and aerosol rainout from the baffle is directed into the trap.

The aerosol generator may have a protector to protect the aerosol generator against physical damage. The protector may include an upper protector above the aerosol generator and/or a lower protector below the aerosol generator, which may be integral with the nebuliser housing. One or more of the protectors may include a mesh.

The nebuliser may include a respiratory connector for connecting the outlet port to a respiratory system. The respiratory connector may include a mouth piece. The respiratory connector may be selected from a group consisting of a mouthpiece, a face mask, and a nasal piece.

In another embodiment the nebuliser include an aerosol generator housing in which the aerosol generator is held. The aerosol generator housing may be fixed to the reservoir.

In another embodiment the aerosol generator may comprise a vibratable member having a plurality of apertures extending between a first surface and a second surface thereof. The apertures in the vibratable member are sized to aerosolise the medicament by ejecting droplets of medicament such that about 70% or more of the droplets by weight have a size in the range from about 1 to about 6 micrometers.

In another embodiment the nebuliser may include a drive circuit for the aerosol generator. The drive circuit may include a push-pull resonant power circuit. The resonant circuit may use an inductive element that has an impedance value substantially equal to the impedance of the piezoelectric element.

The resonant circuit may include an inductive element. For example, the resonant circuit may include a pair of MOSFET switches operated as a push-pull (alternate on-off) arrangement.

The nebuliser drive circuit may be adapted to be plugged directly to a wall outlet receiving an input of an alternating voltage in the range from 90V to 250V at a frequency range from 50 Hz-60 Hz and producing an alternating voltage output at a frequency range from 50 Khz to 300 Khz. The circuit may include an inductive element having substantially the same impedance of the nebuliser circuit at the operating frequency.

In another embodiment, the nebuliser drive circuit may be adapted for use with batteries receiving an input of voltage in the range from 1.5 to 12 Volt and producing an alternating voltage output at a frequency range from 50 Khz to 300 Khz.

The circuit may include an inductive element having substantially the same impedance of the nebuliser circuit at the operating frequency.

Another aspect of the invention includes methods for nebulising a viscous liquid. In one embodiment, a method includes providing a vibratable thin shell member that includes a front surface, a rear surface and a plurality of tapered apertures extending therebetween, the apertures being tapered to narrow from the rear surface to the front surface, vibrating the thin shell member, and sweeping the frequency between two frequency values.

In another embodiment, a method for nebulising a viscous liquid includes providing a vibratable thin shell member that includes a front surface and a rear surface and a plurality of tapered apertures extending therebetween, the apertures being tapered to narrow from rear surface, to the front surface, vibrating the thin shell member, and supplying heat to a viscous liquid (e.g., a lipid).

Another embodiment of the invention provides an aerosol generator that includes an electrical connector for supplying electrical power to the aerosol generator, the electrical connector and the current carrying components of the aerosol generator being encased by electrically insulating material.

Embodiments of the invention also include an aerosol generator assembly that includes an aerosol generator and a power inlet, the assembly being structurally supported by elastomeric encasing, where the encasing may also provide electrical insulation to the assembly. The elastomeric encasing may be produced by a process of injection molding.

In another embodiment of the invention provides an aerosol generator assembly that includes an aerosol generator and a power inlet encased by an elastomeric structure. The aerosol generator may include a vibratory thin shell member having a rear surface and a front surface and a plurality apertures extending therebetween, the apertures having a size range of about 1 to about 6 microns at their smaller opening.

Additional novel features shall be set forth in part in the description that follows, and in part will become apparent to those skilled in the art upon examination of the following specification or may be learned by the practice of the invention. The features and advantages of the invention may be realized and attained by means of the instrumentalities, combinations, and methods particularly pointed out in the appended claims.

BRIEF DESCRIPTION OF THE DRAWINGS

The invention will be more clearly understood from the following description thereof given by way of example, in which.

DETAILED DESCRIPTION OF THE INVENTION

Figure 1:
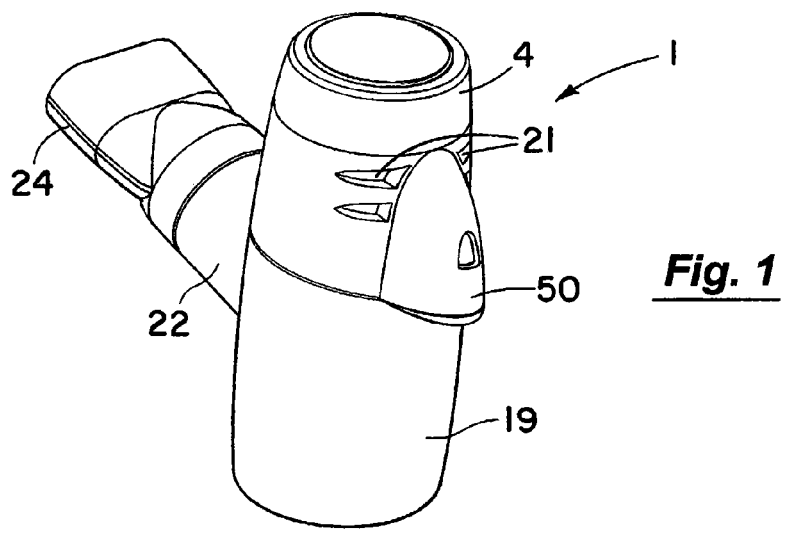
FIG. 1 is a perspective view of a nebuliser according to an embodiment of the invention.

Referring to the drawings and initially to FIGS. 1 to 8 thereof there is illustrated a nebuliser 1 according to an embodiment of the invention for delivery of a medicament to the respiratory system of a patient. The nebuliser 1 comprises a housing having a reservoir, which in this embodiment takes the form of medication cup 2 for liquid medicament. The medication cup 2 has an upper inlet 3 which is covered by a releasable cup 4. The cup 4 is transparent to allow a user to view the contents of the cup. The cup 2 also has a lower outlet to which the medicament flows by gravity. The cup 4 has a lower conical portion 6 to promote the flow of medicament to the outlet. An aerosol generator 7 is mounted at the outlet of the cup to aerosolise the liquid medicament. The aerosol generator 7 is protected against user access from above by a barrier mesh 10 which in this case is integrally formed with the medication cup. The aerosol generator 7 is also protected from below by a lower mesh 11 which is separately formed from the medication cup 2. The protector meshes 10, 11 are particularly apparent from FIGS. 5, 7 and 8.

Aerosol generated by the aerosol generator 7 is delivered into a vented aerosol passage 20 defined by a nebuliser body 19. Air passes into the passage 20 through air inlets 21. The air entrains the aerosolised medicament and the entrained aerosolised medicament is delivered from the nebuliser through an outlet port 22 from the passage 20. In this case the inlets 21 are formed by air vents which are located above the aerosol generator 7. The outlet port 22 has an extension or connector piece 23 which is inclined upwardly to direct flow into a respiratory system. In this case the outlet connector 23 is fitted with a releasable mouthpiece part 24 which is a push-fit on the connector 23.

The nebuliser 1 has a baffle to direct air and entrained aerosolised medicament to the outlet 22. In this case the baffle is formed by a floor 25 of the nebuliser body 19. It will be noted that the baffle 25 is inclined downwardly towards the outlet port 22. The arrangement of the inlet 21 on one side of the nebuliser housing, the outlet 22 on a generally opposite side of the housing and the baffle 25 optimises the flow of air and entrained aerosolised medicament to the outlet 22.

The nebuliser 1 has an aerosol rain-out trap 30 for collecting any larger droplets not entrained in the air. In this case the rain-out trap 30 is between the outlet port 22 and the baffle 25. Any droplets not entrained by the air impinge on the baffle 25 and flow down the incline into the trap 30. Similarly any droplets that may form at the outlet 22 or in the associated connectors are directed to flow into the trap 30. The trap 30 is readily emptied by opening the nebuliser housing and inverting the bottom of the housing.

Typically, the medication cup 2 is configured to accommodate up to about 6 ml to about 10 ml of liquid medicament.

The aerosol generator 7 comprises a vibratable member 40 and a piezoelectric element 41. The vibratable member 40 has a plurality of tapered apertures extending between a first surface and a second surface thereof, as described in U.S. Pat. No. 5,164,740 (the first '740 patent); U.S. Pat. No. 5,586,550 (the '550 patent); U.S. Pat. No. 5,758,637 (the '637 patent); and U.S. Pat. No. 6,085,740 (the second '740 patent), the entire contents of which are incorporated herein by this reference.

The first surface of the vibratable member 40, which in use faces upwardly, receives the liquid medicament from the medication cup 2, and the aerosolised medicament is generated at the second surface of the vibratable member 40 by ejecting droplets of medicament upon vibration of the member 40. In use the second surface faces downwardly. In one case, the apertures in the vibratable member 40 may be sized to produce an aerosol in which about 70% or more of the droplets by weight have a size in the range from about 1 to about 5 micrometers. In another embodiment, about 70% or more (by weight) of the droplets have sizes ranging from about 1 to about 6 micrometers.

The vibratable member 40 is non-planer, and is preferably dome-shaped in geometry.

Figure 9A:
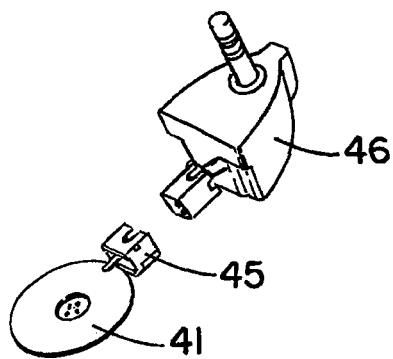
FIGS. 9(a) to 9(d) are perspective views illustrating the mounting and overmoulding of a vibratable member and associated connector for a nebuliser according to an embodiment of the invention.
Figure 9B:
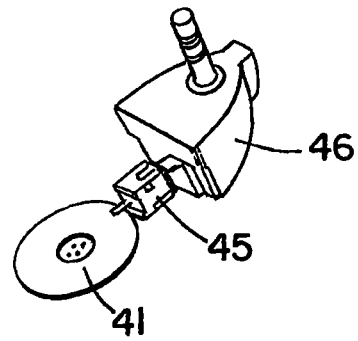
Figure 9C:
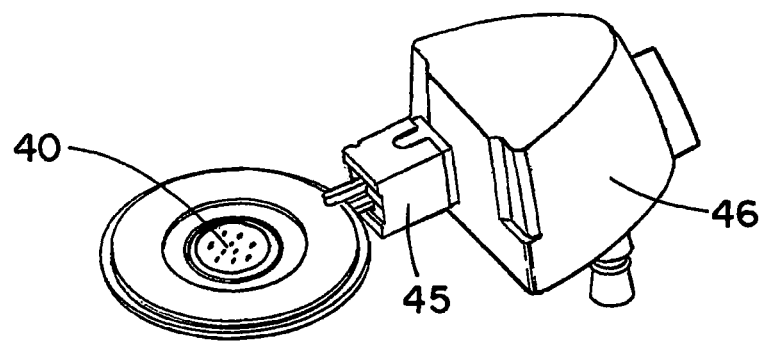
Figure 9D:
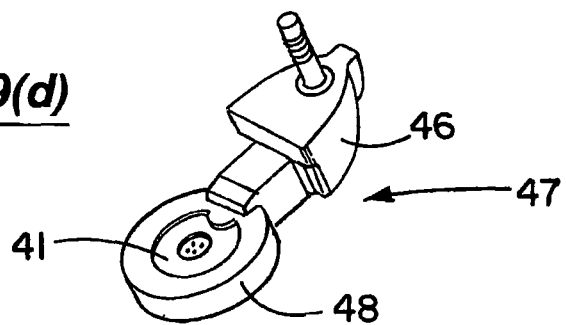

The piezoelectric element 41 has an electrical connection socket 45 to which a connector plug element 46 is mounted as illustrated in FIGS. 9(a) and 9(b). The piezoelectric element 41 and the connection 45 and plug 46 is then overmoulded to form a sub-assembly 47 which defines a housing 48 for the piezoelectric element 41. The sub-assembly 47 is mounted in the nebuliser housing as illustrated.

The apparatus 1 also includes a controller as illustrated, to control operation of and to supply power to the aerosol generator 7. The plug element 46 defines a signal interface port 50 fixed to the nebuliser housing to receive a control signal from the controller. The controller may be connected to the signal interface port 50 by means of a control lead 52, which has a docking member 51 or connector for mating with the plug 46 at the interface port 50. A control signal and power may be passed from the controller through the lead 52 to the aerosol generator 7 to control the operation of and supply power to the aerosol generator 7.

Figure 2:
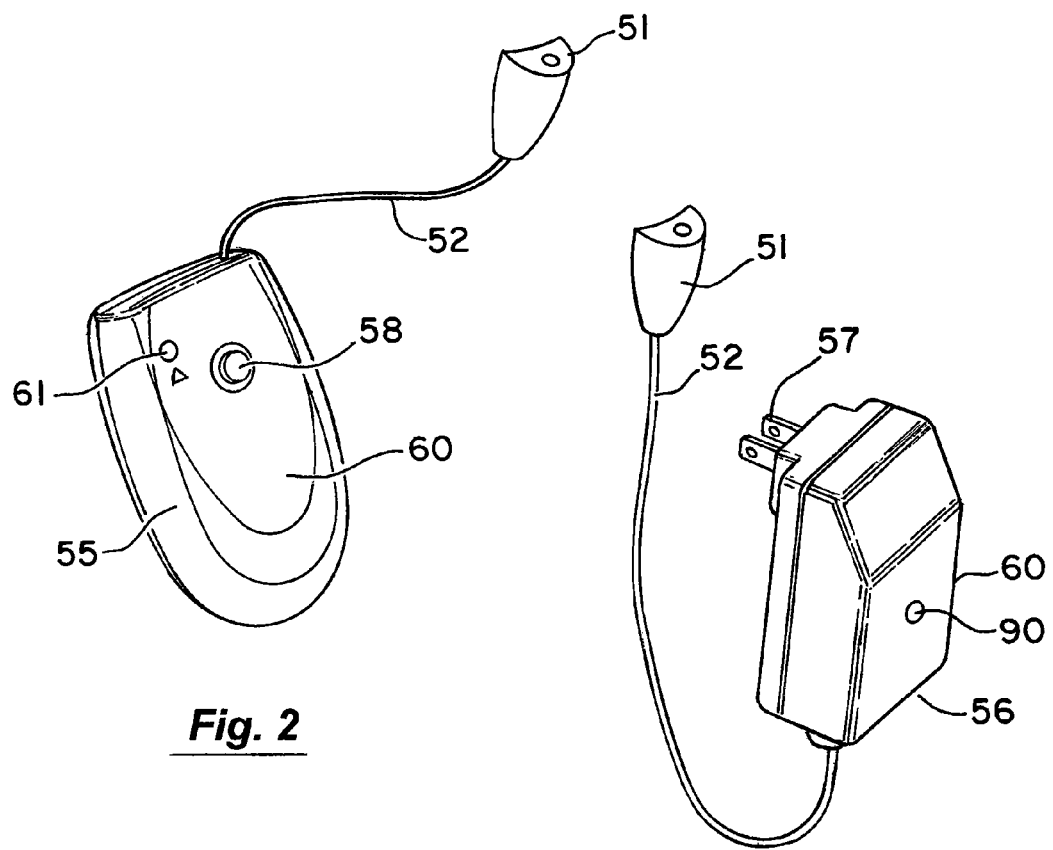
FIG. 2 is a perspective view of a battery driven controller for use with the nebuliser.
Figure 3:
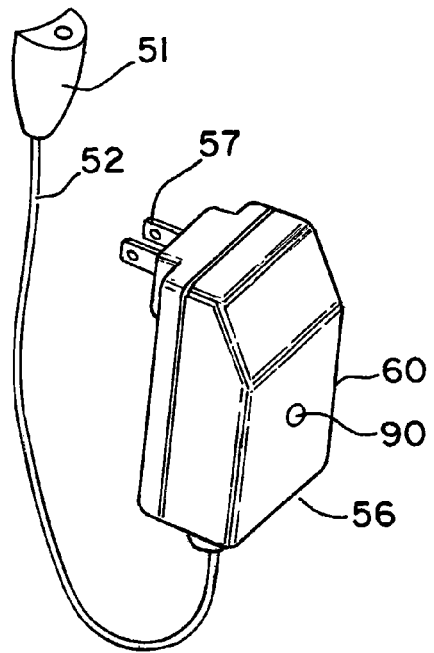
FIG. 3 is a perspective view of a mains driven controller for use with the nebuliser.
Figure 4:
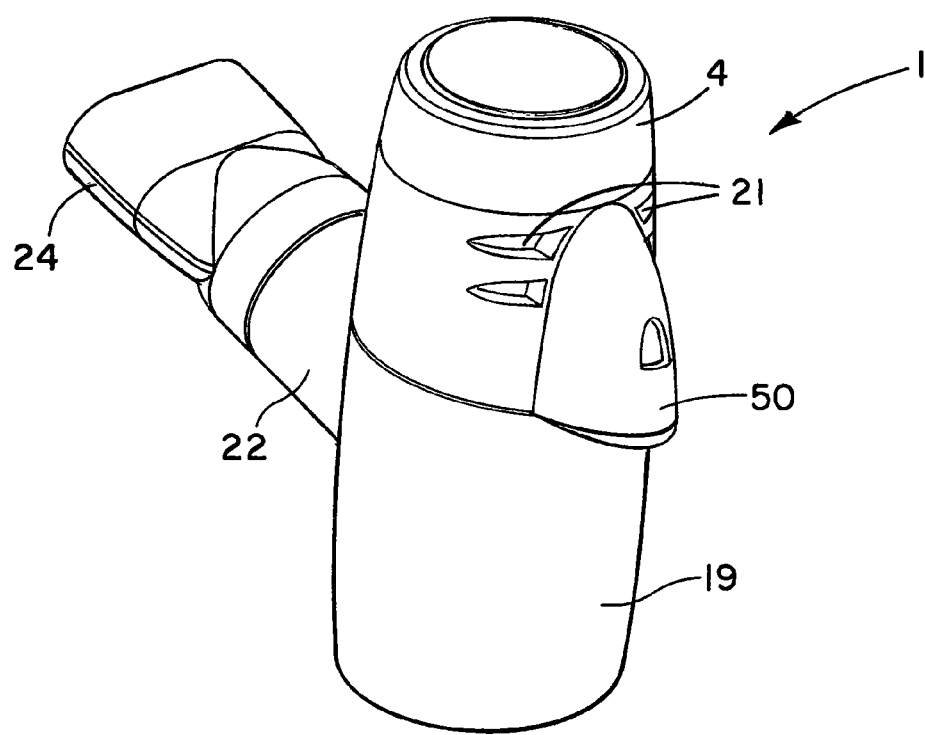
FIG. 4 is a perspective view of a nebuliser according to an embodiment of the invention with a mouth piece fitted.
Figure 5:
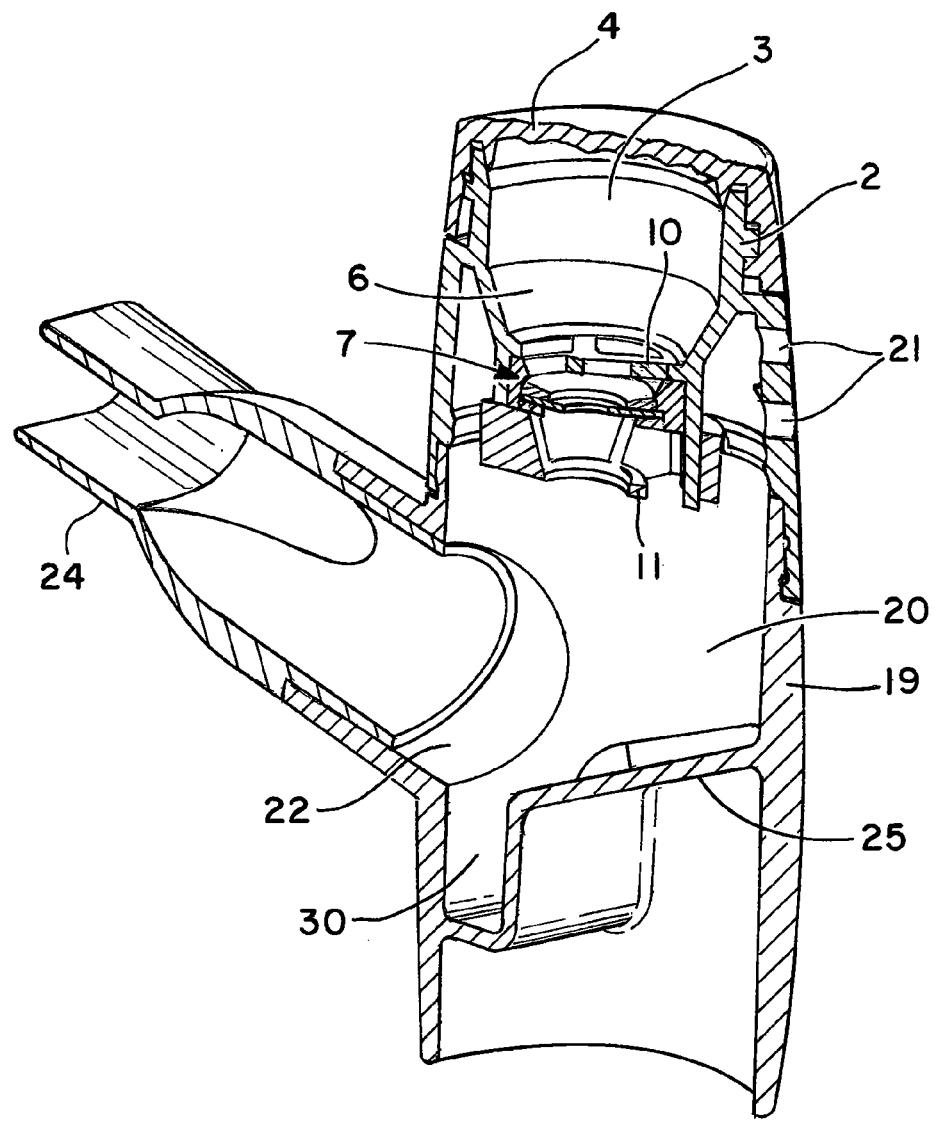
FIG. 5 is a cut-away view of the nebuliser of FIG. 4.
Figure 6:
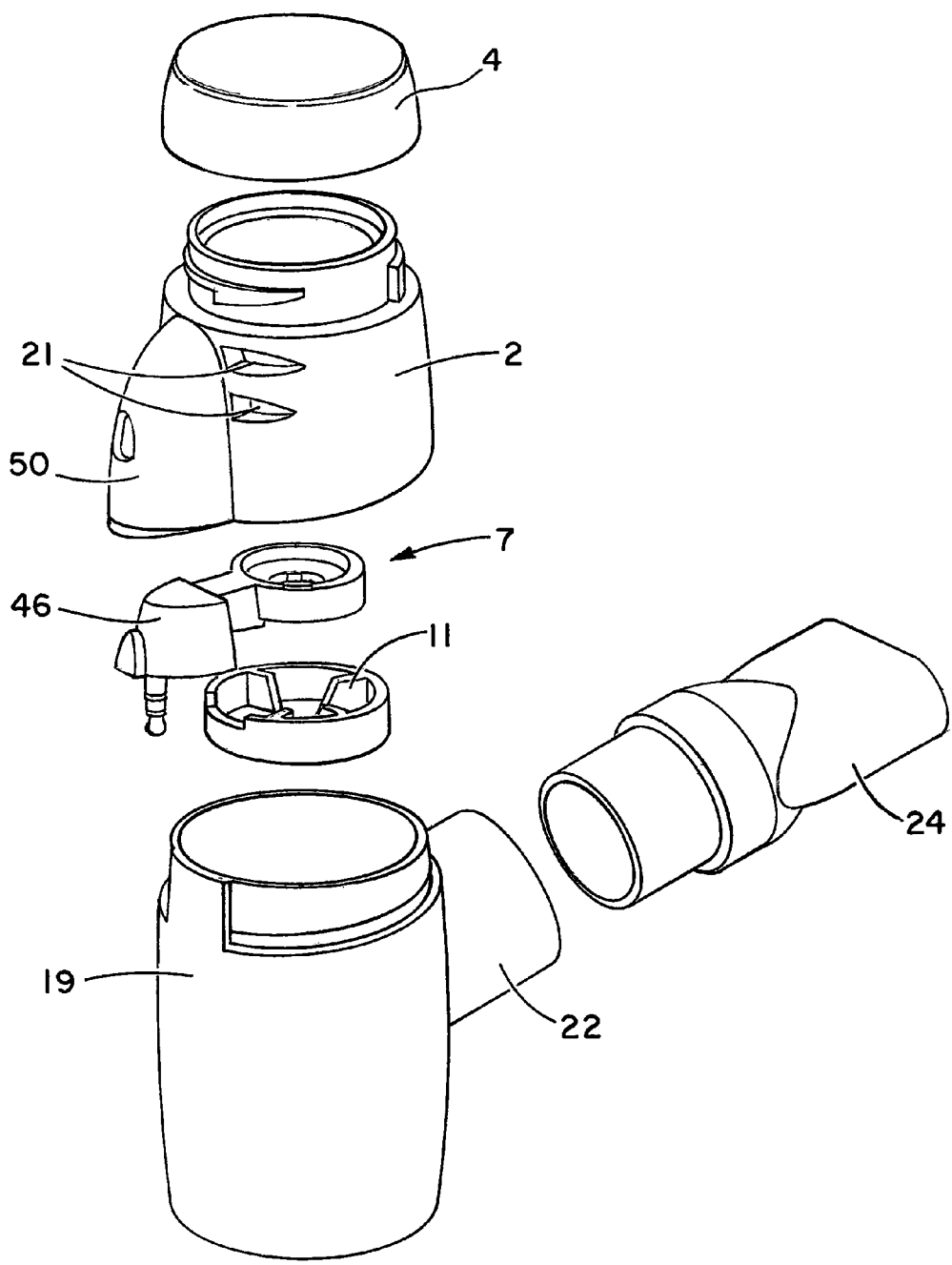
FIG. 6 is an exploded view of the nebuliser of FIGS. 4 and 5.
Figure 7:
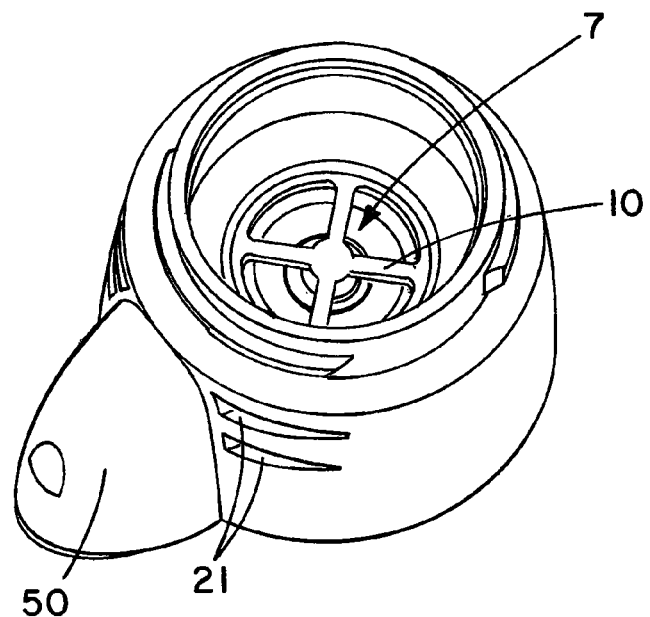
FIG. 7 is a perspective view from above of an upper part of the nebuliser.
Figure 8:
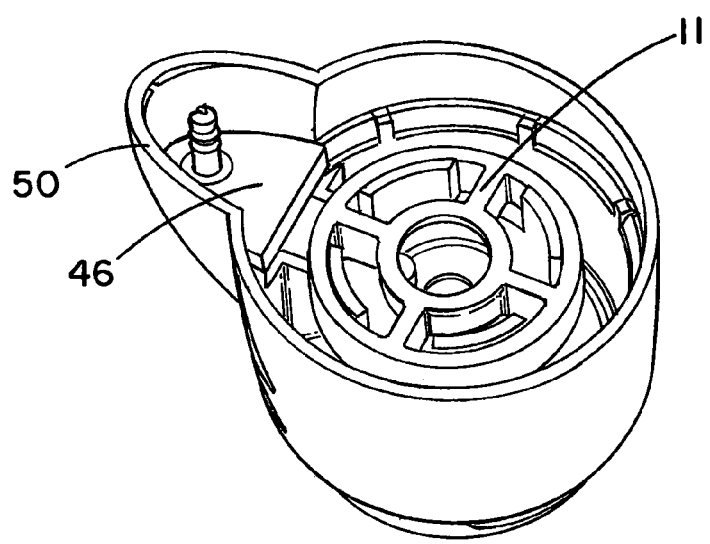
FIG. 8 is a perspective view from below of the upper part of the nebuliser.

As illustrated in FIG. 2 in one case a controller 55 may comprise a battery operated unit.

Alternatively, a controller 56 may have a mains plug 57 for connecting directly to a mains power source. In this case the controller has an integral AC-DC circuit as well as control circuitry mounted in a single housing.

Each controller 55 or 56 has a housing 60 and a user interface to selectively control operation of the aerosol generator 7. The user interface may be in the form of, for example, an on-off button 58.

Status indication means are also provided on the housing 60 to indicate the operational state of the aerosol generator 7. For example, the status indication means may be in the form of a visible LED 61, to indicate an operational state of the aerosol generator 7.

Figure 10:
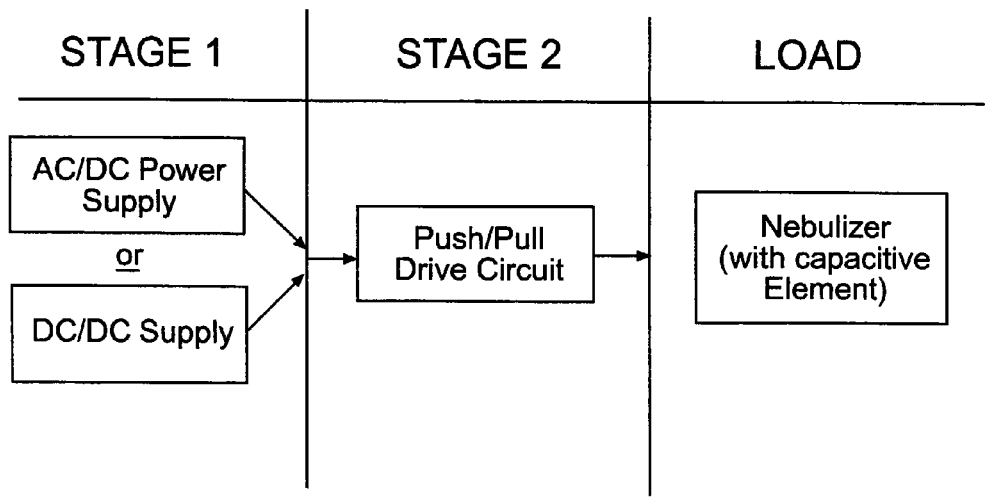
FIG. 10 is a block diagram of a drive for a piezoelectric element.
Figure 11:
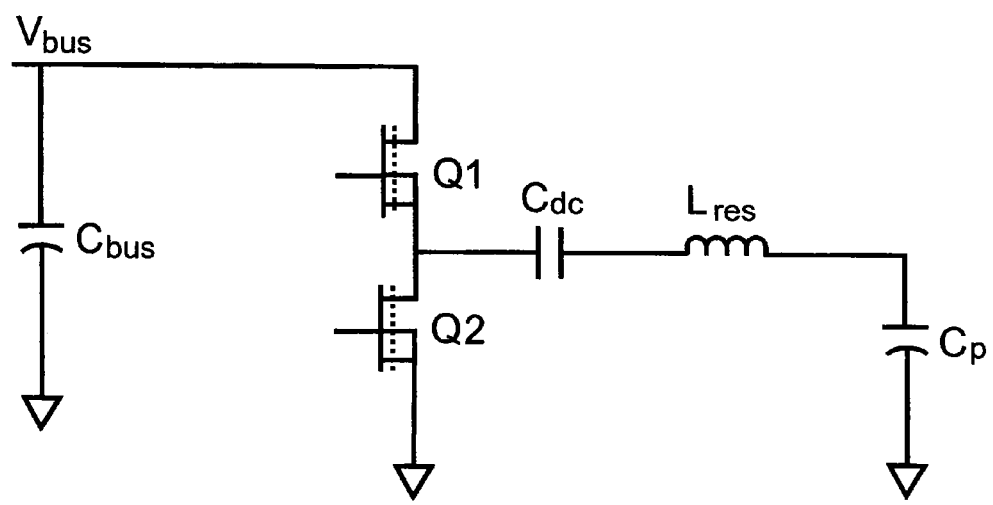
FIG. 11 is a circuit diagram of the drive and load stages of FIG. 10.
Figure 12:
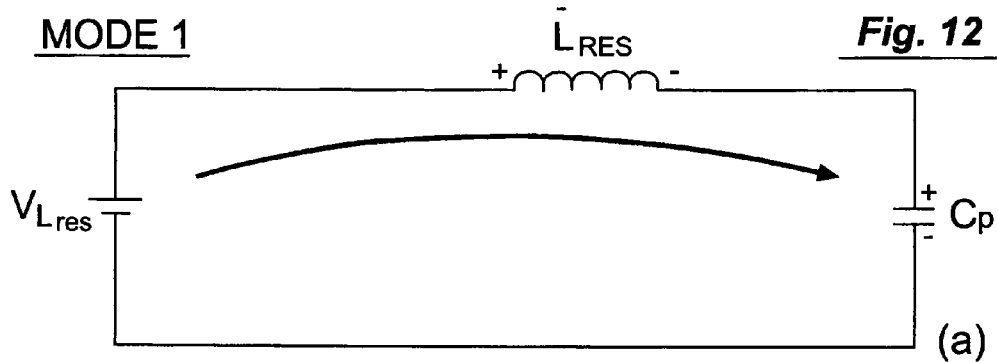
FIGS. 12(a) to 12(d) are circuit diagrams showing operation of the drive of FIGS. 10 and 11 in four modes labelled mode I to mode 4.
Figure 12:
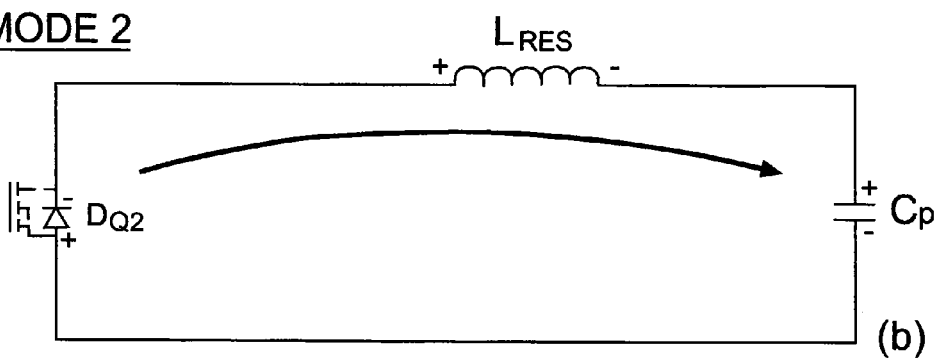
Figure 12:
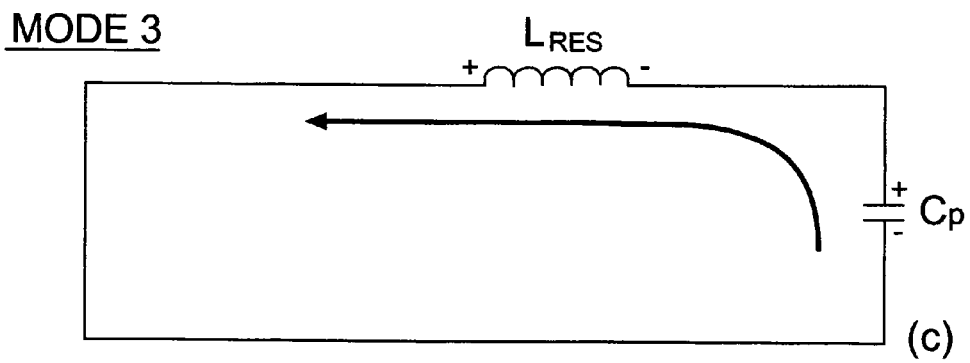
Figure 12:
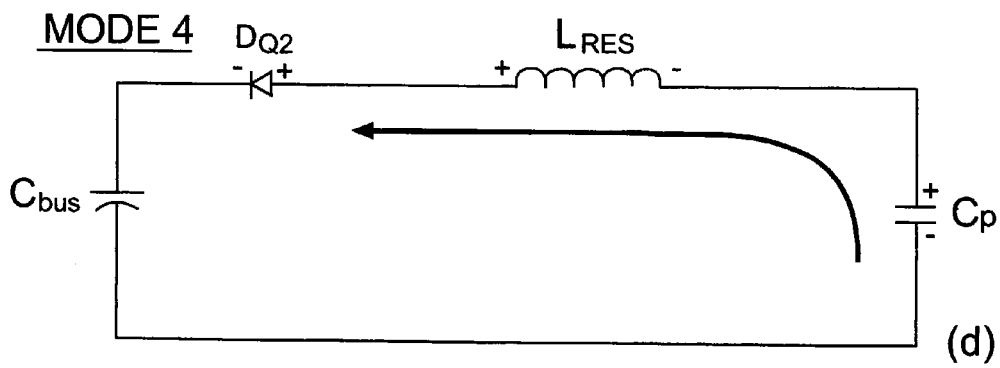

Referring to FIGS. 10 to 12 the piezo drive arrangement is illustrated. Power may be from an AC/DC power supply or a DC/DC power supply, in what is illustrated as a Stage 1. Where the former a $V_{bus}$ level of 20V is provided by a universal input (85 $V_{ac}$–264 $V_{ac}$) AC/DC adapter. Where the latter, batteries may provide the power.

In a Stage 2 a push/pull resonant circuit provides the following output to the load:

$P_{out}$=1 W
$f_{out}$=128 kHz
$V_{out}$=54 $V_{rms}$

The resonant circuit comprises a resonant inductor $L_{res}$ and the capacitive element ($C_p$) of the piezoelectric load, driven by two MOSFETs Q1 and Q2 in a push-pull arrangement. As shown in FIG. 11 the resonant circuit also comprises a 100 μF bulk capacitor $C_{bus}$ and a DC blocking capacitor $C_{dc}$.

Referring particularly to FIGS. 12(a) to 12(d) switching period modes Mode 1 to Mode 4, respectively, are illustrated.

Mode 1
$C_{dc}$ is neglected because its AC ripple is assumed negligible.
Q1 turned on, Q2 turned off.
Positive current flow in direction of arrow.
Mode equations solved using equation:

$$V_{bus}=V_{Lres}+V_{Cp}(t)$$

Mode 2
Q1 turning off, Q2 off.
Current freewheels through anti-parallel diode of Q2.
Mode equation:

$$V_{Lres}(t)+V_{Cp}(t)+V_{DQ2}=0$$

Mode 3
Q1 turned off, Q2 turned on.
Positive current flow in direction of arrow.
Mode equation:

$$V_{Lres}(t)+V_{cp}(t)=0$$

Mode 4
Q2 turning off, Q1 off.
Current freewheels through anti-parallel diode of Q1.
Mode equation:

$$V_{Cp}(t)+V_{Lres}(t)-V_{DQ1}-V_{Cbus}=0$$

In use, the cap 4 is opened and medicament is delivered through the inlet port 3 into the medication cup 2. Typically a supply container, such as a nebule or a syringe, is used to deliver the liquid medicament through the inlet port 3 into the medication cup 2. The liquid medicament in the medication cup 2 flows by gravitational action towards the aerosol generator 7 at the lower medicament outlet.

By distancing the inlet port 11 to the reservoir 2 from the aerosol generator 3 at the outlet 16, this arrangement creates a sterile barrier between the delivery of the liquid medicament into medication cup 2 and the respiratory system of the patient.

The docking member of the control lead 52 is mated with the signal interface port 50 on the reservoir 2 to connect the controller 55 or 56 to the aerosol generator 7. The controller 50 may then be activated to supply power and a control signal to the aerosol generator 7, which causes the piezoelectric element 41 to vibrate the vibratable member 40.

This vibration of the vibratable member 40 causes the liquid medicament at the top surface of the member 40 to pass through the apertures to the lower surface where the medicament is aerosolised by the ejection of small droplets of medicament.

The aerosolised medicament passes from the aerosol generator 7 into the passage 20 of the housing 19. The aerosolised medicament is entrained with a gas, such as air, which passes into the passage 20 through the inlet 21. The entrained mixture of the aerosolised medicament and the gas then passes out through the outlet 22 and on to the respiratory system of the patient.

In this case, the mouthpiece 24 is gripped between the teeth of the user, with the lips sealed around the mouthpiece. The user breathes in and out slowly. On the exhale cycle, exhaled gas flows back along the mouthpiece and into the passage 20. Exhaust may pass through the gas inlets 21. Breathing is continued in this way until aerosol formation has stopped indicating that all the medicament in the medication cup 2 has been delivered into the patients respiratory system. The nebuliser is turned off by pressing the on/off button 58.

A suitable material for the various connectors and housings is ABS. An alternative material for the various connectors and housings is polycarbonate or polysulphone. By manufacturing these components of the apparatus from polysulphone or polycarbonate, this enables these components to be autoclaved for multiple use of the same apparatus.

Figure 13:
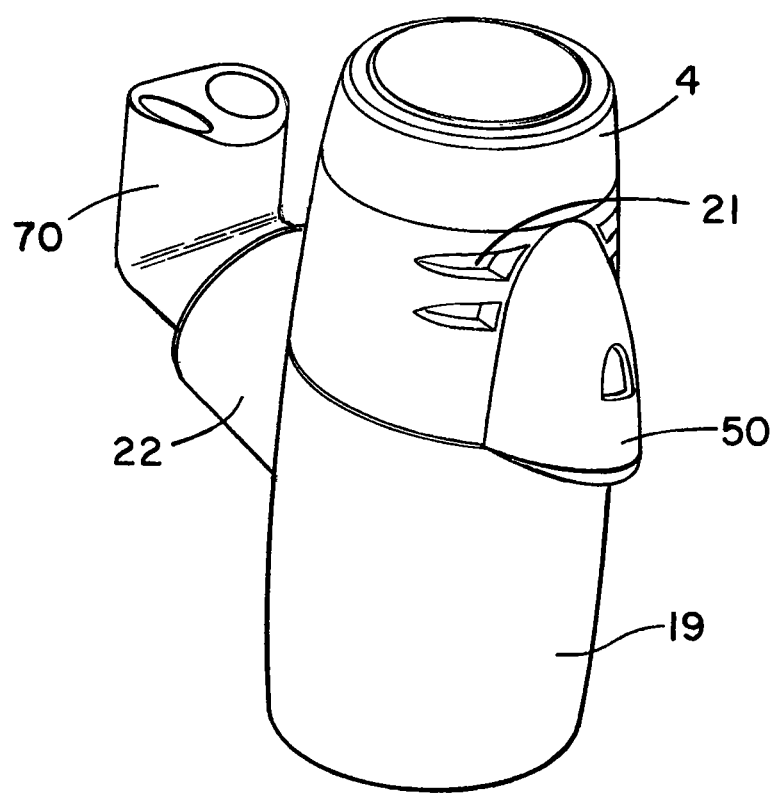
FIGS. 13 to 15 are views similar to FIGS. 4 to 6 of a nebuliser according to an embodiment of the invention that includes a nasal piece fitted.
Figure 14:
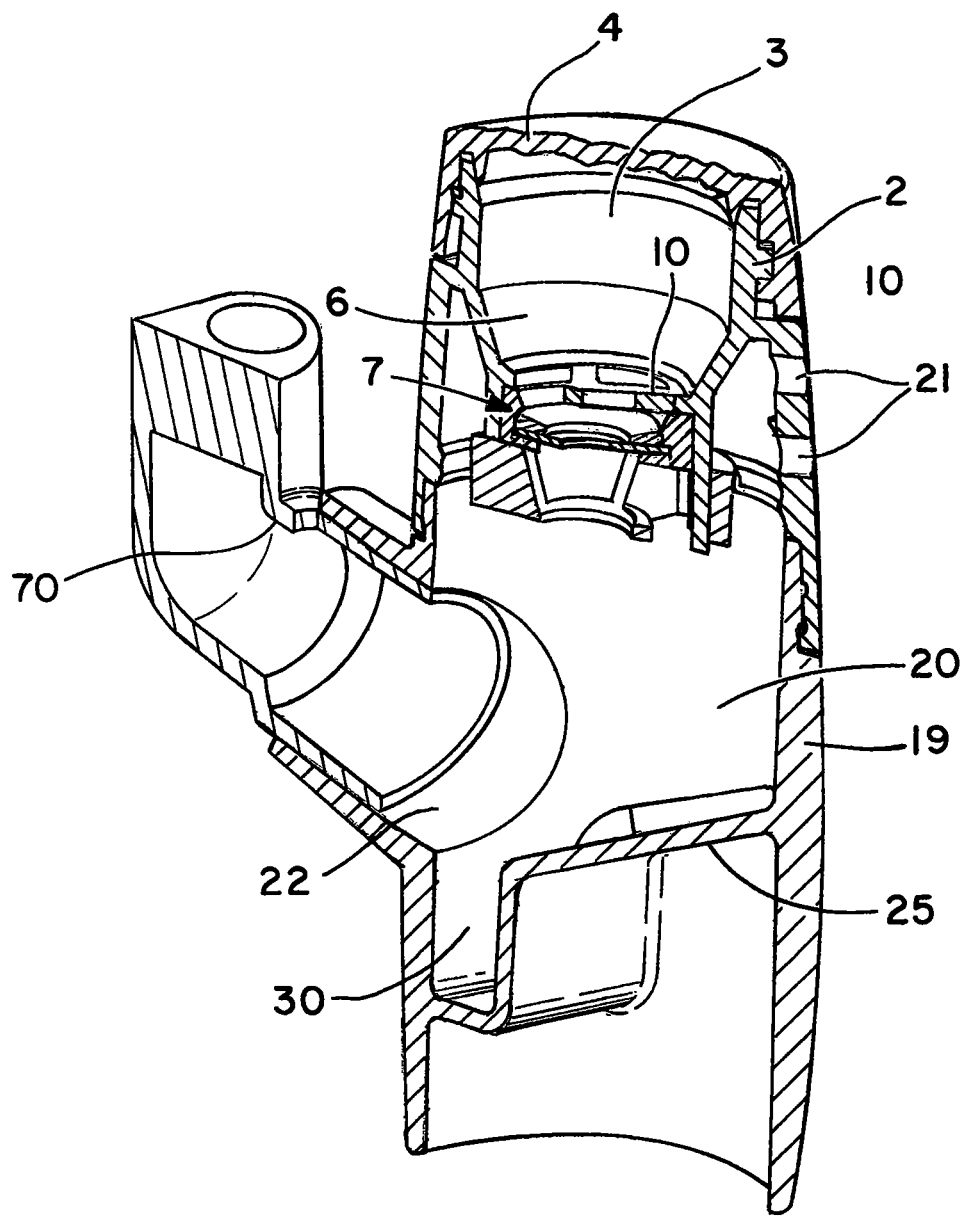
Figure 15:
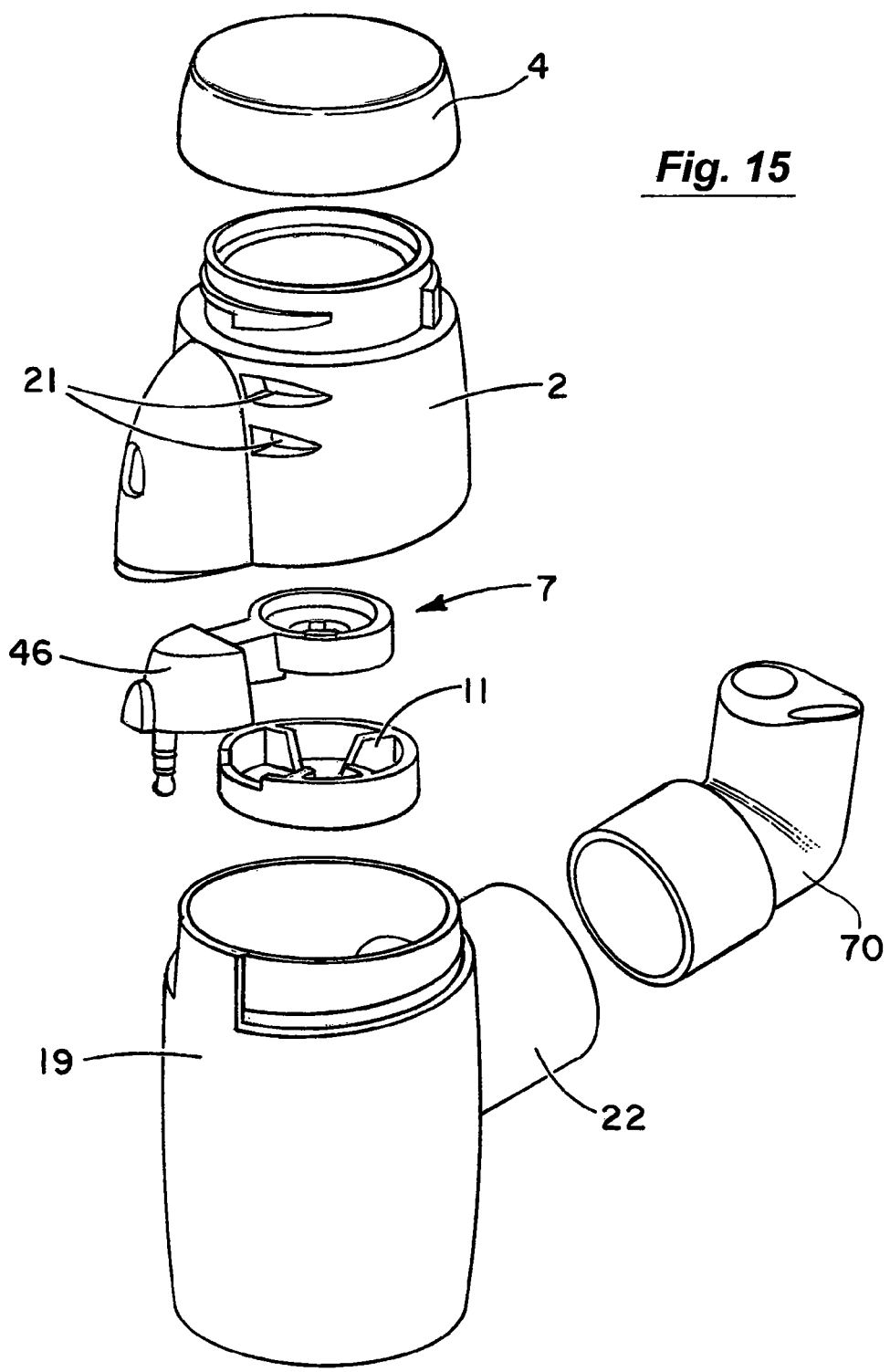

Referring now to FIGS. 13 to 15 there is illustrated a nebuliser as described above with a nasal piece 70 attached. The nasal piece 70 is used to deliver the medicament through the users nose.

Figure 16:
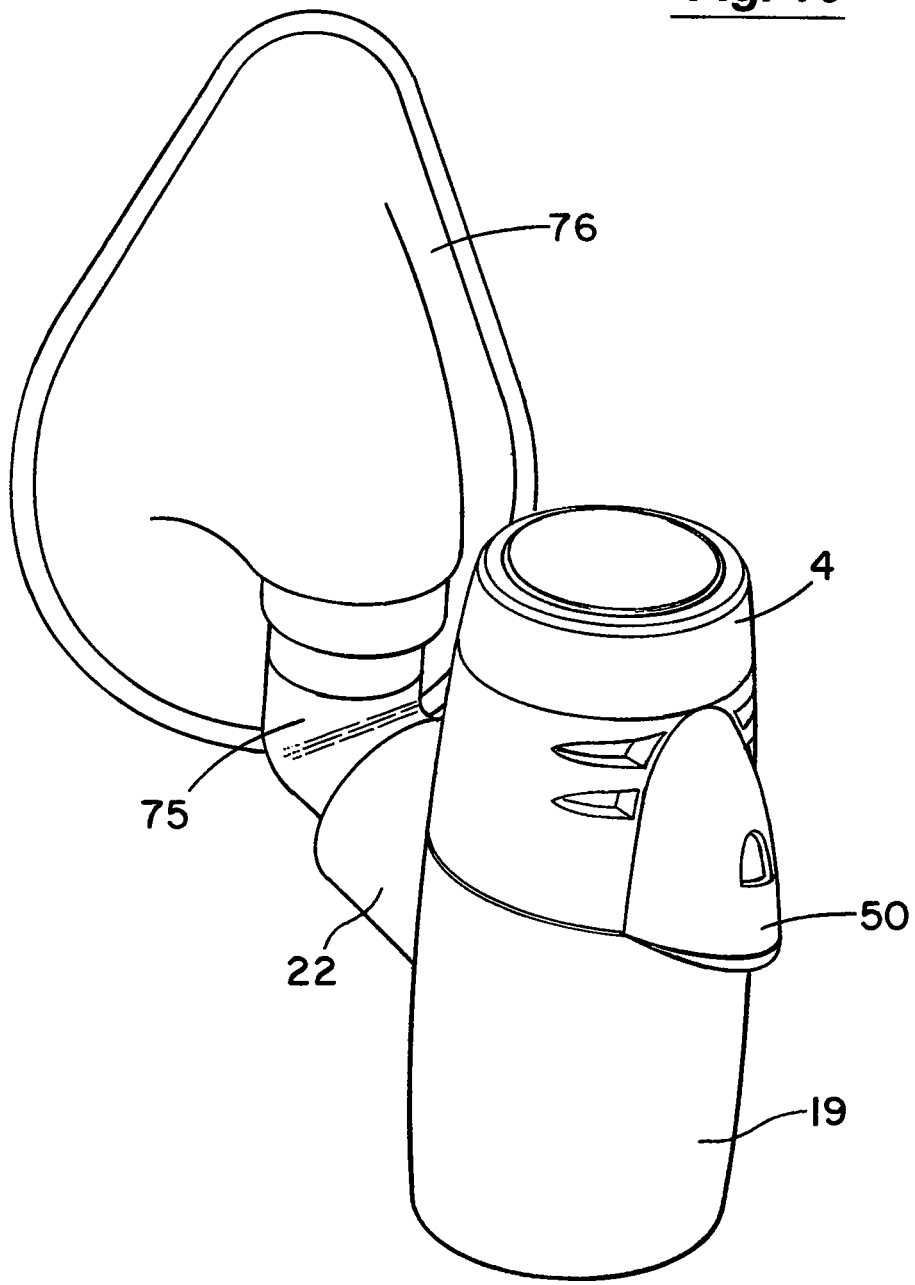
FIGS. 16 to 18 are views similar to FIGS. 4 to 6 of a nebuliser according to an embodiment of the invention with a face mask adaptor fitted.
Figure 17:
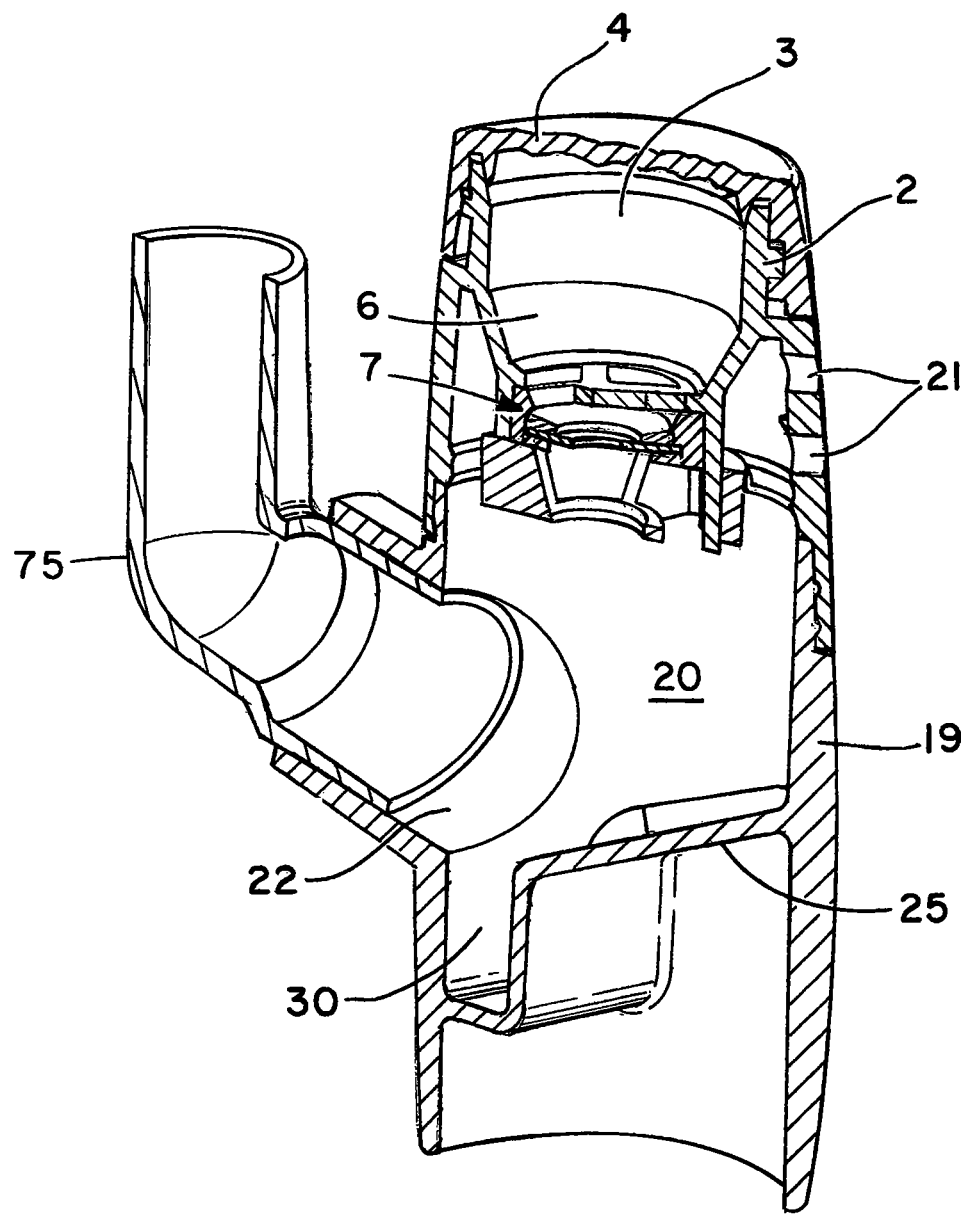
Figure 18:
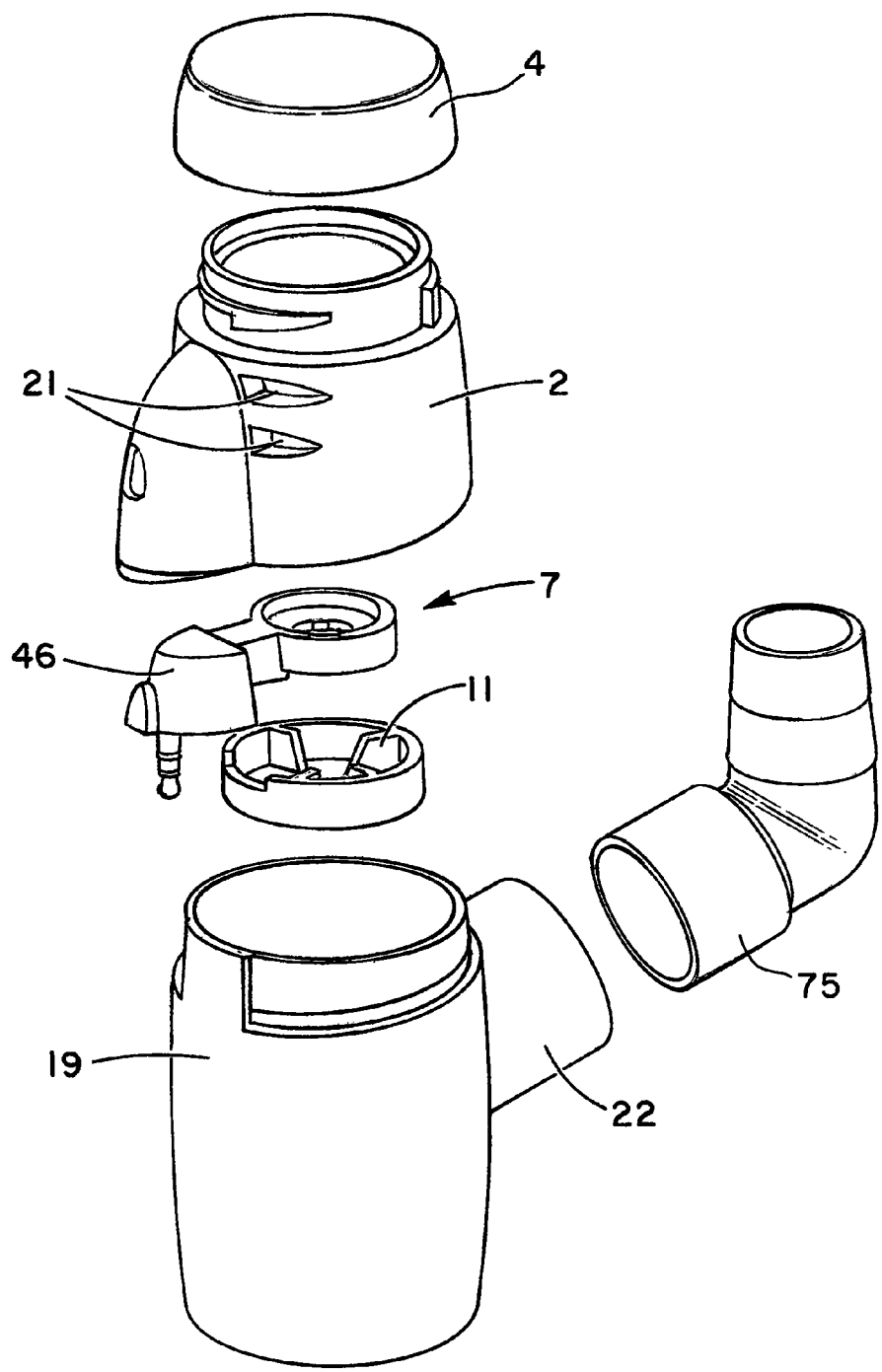

Referring now to FIGS. 16 to 18 there is illustrated a nebuliser as described above which in this case has an elbow connector 75 for connection to a face mask 76.

Figure 19:
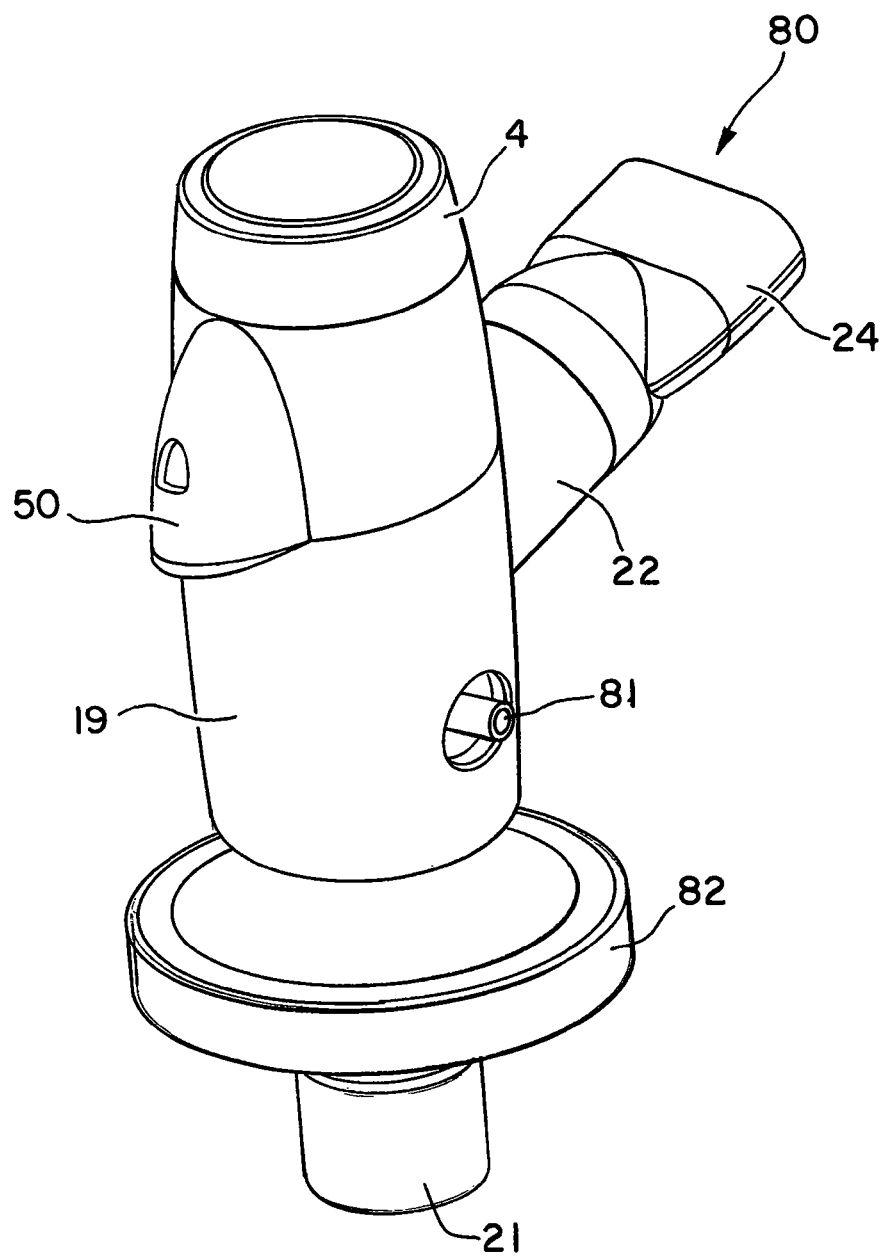
FIGS. 19 to 21 are views similar to FIGS. 4 to 6 of a nebuliser according to another embodiment of the invention.
Figure 20:
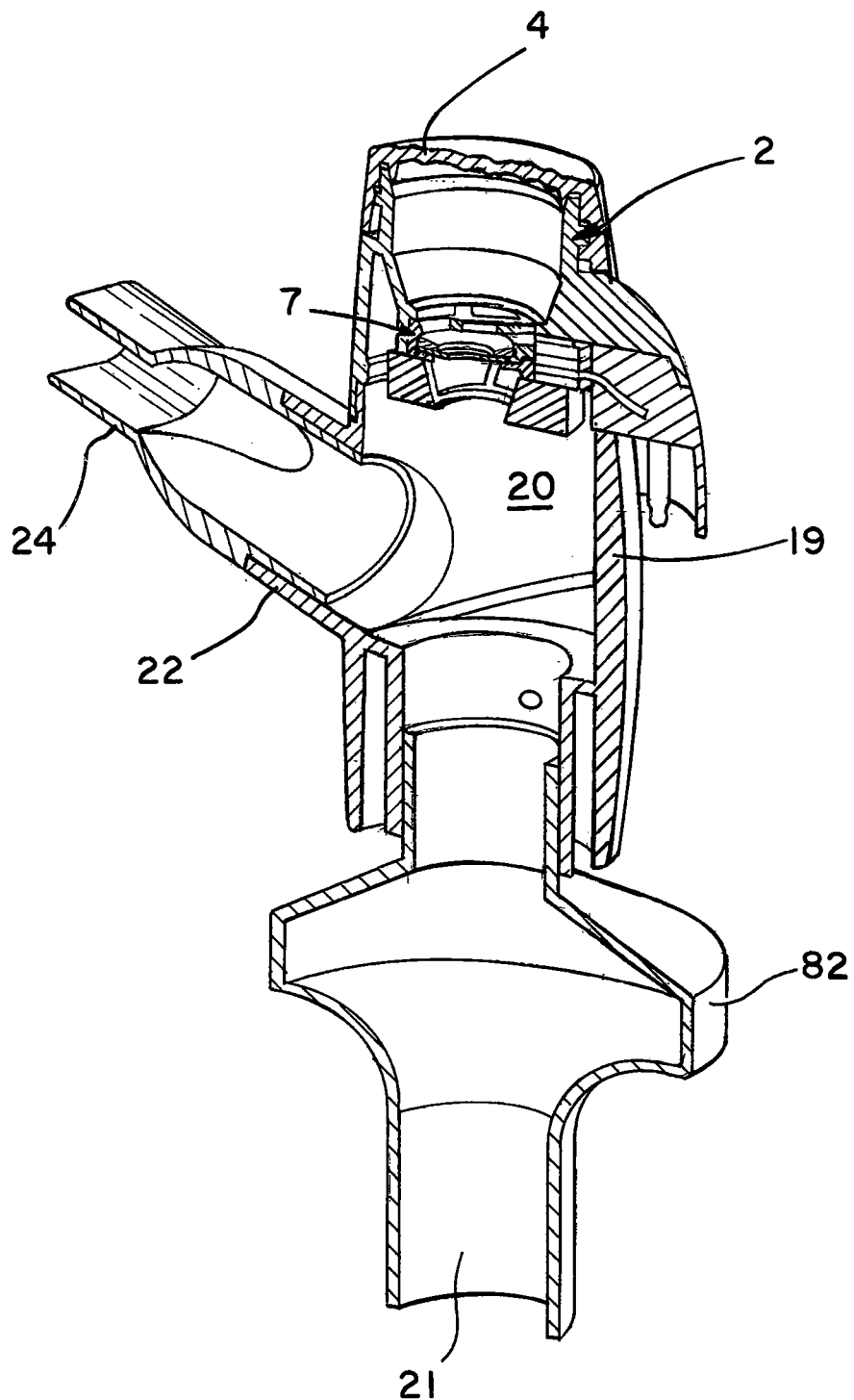
Figure 21:
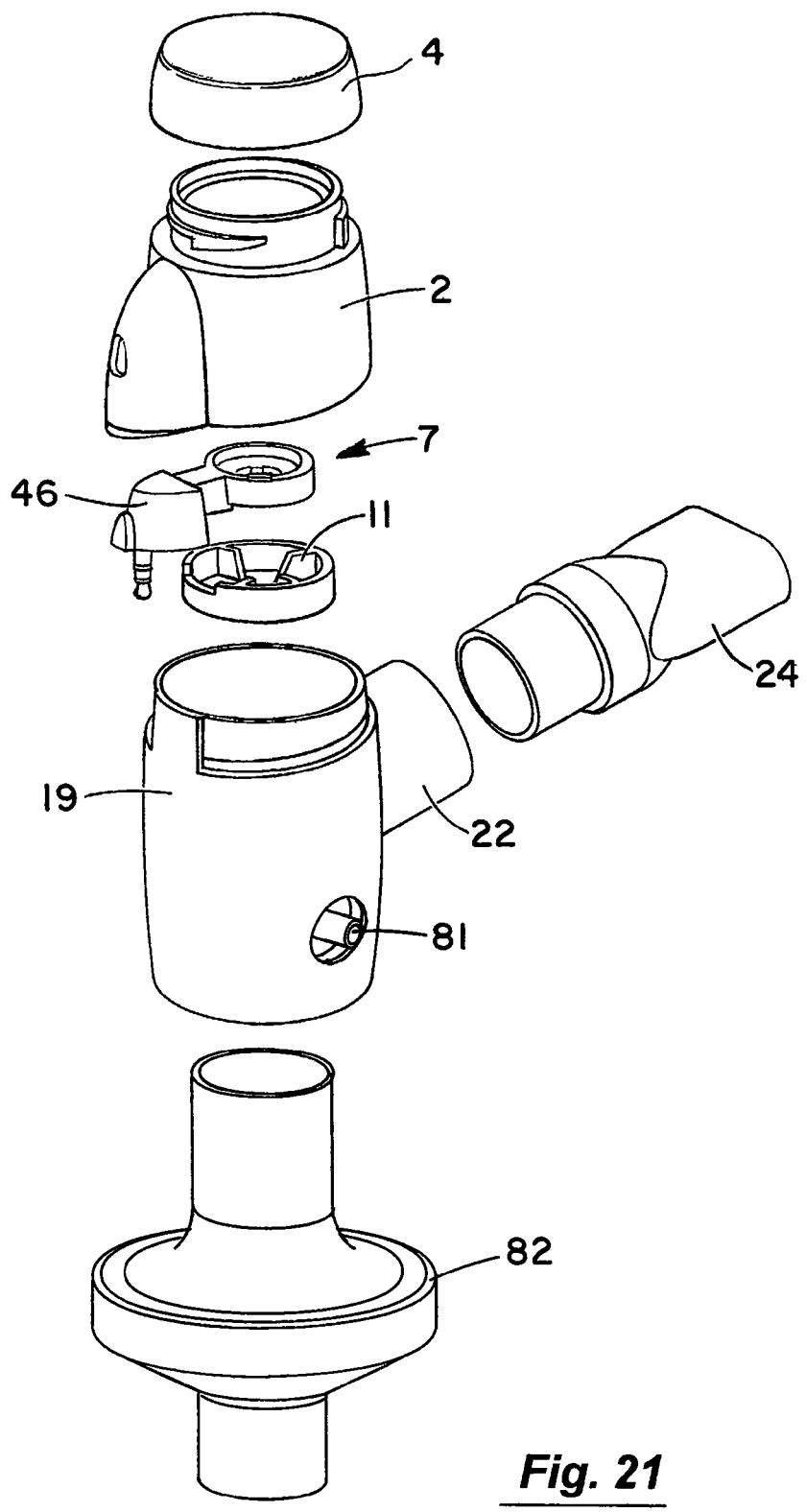

Referring to FIGS. 19 to 20 there is illustrated another nebuliser 80 which is similar in some respects to the nebulisers described above and like parts we assigned the same reference numerals. In this case air is supplemented by an oxygen supply which is connected through an inlet port 81. A holder 82 is releasably mounted to the nebuliser housing. The holder accepts an external filter which collects all exhaled aerosol. In addition, the holder serves as a diffuser to the jet of gas entering through the inlet port, reducing turbulence and impactive losses of aerosol within the nebuliser housing.

The invention provides a nebuliser which is relatively small, light weight and is easy to use. The controllers are also small and light weight. Aerosol is readily generated and efficiently entrained in a gas flow for ease and-efficiency of patient use without medical supervision. The nebuliser may be tilted significantly from the vertical (by up to 45°) without significantly effecting functionality. Thus, the nebuliser may be easily used by patients whilst sitting down or at least partially lying down. The gravity dependent orientation of the aerosol generator and the internal volume in the nebuliser provided by the chamber increases inhaled mass of aerosol in such a way that cough reflex is inhibited. The inclusion of the filter in a dependent position reduces risk of second hand aerosol exposure.

We have found that delivery of non-newtonian fluids can be aided by sweeping the driving frequency of the piezo across the aperture plates' delivery range. It is thought that the aperture plate alters its mode of vibration depending on the drive frequency. This change of motion applies additional stresses to the fluid which can thin it. The frequency sweep may be achieved by using one of the PWM (pulse width modulation) outputs of the microcontroller and routing this signal to the input of a half bridge or MOSFET driver.

In this method the frequency changes by the resolution of the system clock (in our case it is $T_{osc}/4$–20 Mhz crystal/14=5 Mhz. $T=1/F_{osc}=0.2$ μsec. So at approx 130 Khz the frequency can change by approx 3 kHz for each step.) The delivery range is about 120 kHz to 135 kHz. The rate of change of the sweep and range may be controlled using software in the micro controller.

The invention is not limited to the embodiments hereinbefore described which may be varied in construction and detail.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups.

What is claimed is:

1. A nebuliser to deliver a medicament comprising:
   a housing having a reservoir for the medicament;
   an aerosol generator comprising a vibratable member having a plurality of apertures extending between a first surface and second surface of the member that can be supplied the medicament from the reservoir, wherein the generator aerosolizes at least a portion of the medicament into an aerosol;
   a gas venting inlet to permit a gas to enter the nebuliser and form a mixture with the aerosol;
   a passage through which the mixture of the aerosol and the gas is delivered to an outlet port of the nebulizer; and
   a drive circuit for the aerosol generator;
   wherein the drive circuit is configured to, substantially throughout aerosolization, repeatedly change a frequency of vibration of the vibratable member between a first frequency and a second frequency.

2. A nebuliser according to claim 1, wherein the medicament is supplied from the reservoir to the aerosol generator by gravitational flow.

3. A nebuliser according to claim 1, wherein the gas venting inlet is located in close proximity to the aerosol generator.

4. A nebuliser according to claim 1, wherein the housing has a baffle to direct the mixture of the gas and the aerosol to the outlet port.

5. A nebuliser according to claim 4, wherein the baffle comprises an inclined surface oriented to cause aerosol to flow through the outlet port.

6. A nebuliser according to claim 4, wherein the baffle is inclined towards the outlet port.

7. A nebuliser according to claim 1, wherein the nebuliser comprises an aerosol rainout trap.

8. A nebuliser according to claim 7, wherein the rainout trap is adjacent to the outlet port.

9. A nebuliser according to claim 1, wherein the aerosol generator has a protector to protect the aerosol generator against physical damage.

10. A nebuliser according to claim 9, wherein the protector comprises an upper protector above the aerosol generator.

11. A nebuliser according to claim 10 wherein the upper protector comprises a mesh.

12. A nebuliser according to claim 9, wherein the protector comprises a lower protector below the aerosol generator.

13. A nebuliser according to claim 12 wherein the lower protector comprises a mesh.

14. A nebuliser according to claim 12, wherein the lower protector is integral with the nebuliser housing.

15. A nebuliser according to claim 1, wherein the nebuliser comprises a respiratory connector configured to connect the outlet port to a respiratory system.

16. A nebuliser according to claim 15, wherein the respiratory connector comprises a mouth piece.

17. A nebuliser according to claim 15, wherein the respiratory connector is selected from a group consisting of a mouthpiece, a face mask, and a nasal piece.

18. A nebuliser according to claim 1, wherein the nebuliser comprises an aerosol generator housing in which the aerosol generator is held.

19. A nebuliser according to claim 18, wherein the aerosol generator housing is fixed to the reservoir.

20. A nebuliser according to claim 1, wherein the apertures in the vibratable member are sized to aerosolize the medicament by ejecting droplets of medicament such that about 70% or more of the droplets by weight have a size in the range from about 1 to about 6 micrometers.

21. A nebuliser according to claim 1, wherein the drive circuit comprises a push-pull resonant power circuit.

22. A nebuliser according to claim 21, wherein the vibratable member comprises a piezoelectric element and the push-pull resonant power circuit comprises an inductive element having an impedance value substantially equal to an impedance of the piezoelectric element.

23. A nebuliser according to claim 21, wherein the push-pull resonant power circuit comprises an inductive element.

24. A nebuliser according to claim 21, wherein the push-pull resonant power circuit comprises a pair of MOSFET switches operated in an on-off arrangement.

25. A nebuliser according to claim 1, comprising an electrical connector for supplying electrical power to the aerosol generator.

26. A nebuliser according to claim 1, comprising an aerosol generator assembly that includes a power inlet coupled to the aerosol generator, wherein at least a portion of the assembly is encased by an electrically insulating elastomeric casing.

27. A nebuliser according to claim 26, wherein the elastomeric encasing is produced by a process of injection molding.

28. A nebuliser according to claim 1, wherein the nebuliser comprises a drive circuit coupled to the aerosol generator and adapted to be plugged directly to a wall outlet receiving an input of an alternating voltage in the range from about 90V to about 250V at a frequency from about 50 Hz to about 60 Hz, and producing an alternating voltage output at an operating frequency range from about 50 Khz to about 300 Khz.

29. A nebuliser according to claim 28, wherein the drive circuit includes an inductive element having a substantially same impedance of the nebuliser circuit at at least one operating frequency.

30. A nebuliser according to claim 1, wherein the nebuliser comprises a drive circuit coupled to the aerosol generator adapted for use with batteries receiving an input of voltage in the range from 1.5 to 12 Volt and producing an alternating voltage output at an operating frequency range from 50 Khz to 300 Khz.

31. A nebuliser according to claim 30, wherein the drive circuit comprises an inductive element having a substantially same impedance of said nebuliser circuit at at least one operating frequency.

32. A nebuliser according to claim 1, wherein the gas entering the nebuliser comprises air.

33. A method for nebulising a liquid comprising:
providing a vibratable thin shell member comprising a front surface, a rear surface and a plurality of tapered apertures extending therebetween, said apertures being tapered to narrow from the rear surface to the front surface;
vibrating the thin shell member; and
substantially throughout nebulisation, repeatedly sweeping a frequency of vibration of the vibrating thin shell member across a delivery range of the vibratable member.

34. A method according to claim 33, wherein changing a frequency of vibration of the vibrating thin shell member comprises changing a drive frequency of a drive circuit that controls the frequency of vibration of the vibrating thin shell, wherein the drive frequency goes from a first drive frequency to a second drive frequency in a plurality of incremental steps.

35. A method according to claim 33, wherein the liquid is a lipid.

36. A method for nebulising a liquid comprising:
providing a vibratable thin shell member comprising a front surface and a rear surface and a plurality of tapered apertures extending therebetween, said apertures being tapered to narrow from rear surface, to the front surface;
vibrating the thin shell member;
substantially throughout nebulisation, repeatedly sweeping a frequency of vibration of the vibrating thin shell member across a delivery range of the vibratable member; and
supplying heat to the liquid.

37. A method according to claim 36, wherein the liquid is a lipid..

* * * * *